United States Patent
Xie et al.

(10) Patent No.: US 10,676,442 B2
(45) Date of Patent: Jun. 9, 2020

(54) SALT DERIVATIVE OF TETRAHYDROISOQUINOLINE AND CRYSTALLINE THEREOF AND PREPARATION METHOD THEREFORE AND APPLICATION THEREOF

(71) Applicants: CHINA STATE INSTITUTE OF PHARMACEUTICAL INDUSTRY, New Area Shanghai (CN); SHANGHAI INSTITUTE OF PHARMACEUTICAL INDUSTRY, Shanghai (CN)

(72) Inventors: Meihua Xie, Shanghai (CN); Fuli Zhang, Shanghai (CN); Taizhi Wu, Shanghai (CN); Jialiang Zhong, Shanghai (CN)

(73) Assignees: China State Institute of Pharmaceutical Industry, Pudong, New Area Shanghai (CN); Shanghai Institute of Pharmaceutical Industry, Shanghai (CN)

( * ) Notice: Subject to any disclaimer, the term of this patent is extended or adjusted under 35 U.S.C. 154(b) by 0 days.

(21) Appl. No.: 16/329,685

(22) PCT Filed: Aug. 30, 2017

(86) PCT No.: PCT/CN2017/099549
§ 371 (c)(1),
(2) Date: Feb. 28, 2019

(87) PCT Pub. No.: WO2018/041112
PCT Pub. Date: Mar. 8, 2018

(65) Prior Publication Data
US 2019/0177277 A1   Jun. 13, 2019

(30) Foreign Application Priority Data

Aug. 31, 2016 (CN) .......................... 2016 1 0786945
Aug. 31, 2016 (CN) .......................... 2016 1 0786957

(51) Int. Cl.
*C07D 217/18* (2006.01)
*A61P 9/06* (2006.01)
*A61K 31/472* (2006.01)

(52) U.S. Cl.
CPC .......... *C07D 217/18* (2013.01); *A61K 31/472* (2013.01); *A61P 9/06* (2018.01); *C07B 2200/13* (2013.01)

(58) Field of Classification Search
CPC .......................... C07D 217/18; C07B 2200/13
See application file for complete search history.

(56) References Cited

FOREIGN PATENT DOCUMENTS

| CN | 1566098 A | 1/2005 |
|---|---|---|
| CN | 101619038 A | 1/2010 |
| CN | 104693115 A | 6/2015 |

OTHER PUBLICATIONS

RAN. Chinese Journal of Medicinal Chemistry, 2007, 17(2), 65-71 (Year: 2007).*
International Search Report and Written Opinion received in PCT Application No. PCT/CN2017/099549, dated Nov. 27, 2017.

* cited by examiner

*Primary Examiner* — Noble E Jarrell
(74) *Attorney, Agent, or Firm* — Knobbe, Martens, Olson & Bear, LLP

(57) ABSTRACT

The present invention discloses a salt derivative of 1-(3-methanesulfonamidobenzyl)-6-methoxy-7-benzyloxy-1,2,3,4-tetrahydroisoquinoline. The salt derivative has a solubility in water of not less than 3.0 nmol/mL or 1.8 mg/mL.
The salt derivative has a solubility in water of not less than 3.0 nmol/mL or 1.8 mg/mL.

24 Claims, 26 Drawing Sheets

SALT DERIVATIVE OF TETRAHYDROISOQUINOLINE AND CRYSTALLINE THEREOF AND PREPARATION METHOD THEREFORE AND APPLICATION THEREOF

CROSS-REFERENCED TO RELATED APPLICATIONS

This application is a U.S. National Phase Application of PCT International Application No. PCT/CN2017/099549, filed on Aug. 30, 2017, designating the United States of America and published in the Chinese as WO 2018/041112 on Mar. 8, 2018, which claims priority to Chinese Application No. CN201610786945.X, filed Aug. 31, 2016, and Chinese Application No. CN201610786957.2, filed Aug. 31, 2016, the entire contents of which are incorporated herein by reference.

TECHNICAL FIELD

The present disclosure relates to a salt derivative of 1-(3-methanesulfonamidobenzyl)-6-methoxy,7-benzyloxy-1,2,3,4-tetrahydroisoquinoline and its preparation, as well as a pharmaceutical composition comprising same.

BACKGROUND

Sudden cardiac death (SCD) is a leading cause of deaths from cardiovascular diseases. SCD is resultant from regular loss of heart rhythm due to myocardial electrophysiological instability such as sustained ventricular tachycardia (VT) and ventricular fibrillation (VF) which are the most serious cases.

Antiarrhythmic drugs can be divided into four classes. Class I are sodium channel blockers, which can be further divided into subtypes a, b and c, wherein Class Ia, as represented by Quinidine, moderately block the sodium channel; Class Ib, as represented by Lidocaine, block the sodium channel in a milder way and Class Ic, as represented by Flecainide, significantly block the sodium channel. Class II are β-adrenoreceptor blockers, as represented by Propranolol. Class III, as represented by Amiodarone, selectively prolong the repolarization process including action potential duration (APD) and effective refractory period (ERP). Class IV, as represented by Verapamil, are calcium antagonists.

Isoquinoline alkaloids are widely found in natural plants. Certain isoquinoline alkaloids, like bisbenzylisoquinoline alkaloids (eg, berbamine, dauricine, tetrandrine, cocculine, neferine) and monobenzylisoquinoline alkaloids (such as higenamine) and protoberberine (Huangliansu), have cardiovascular activities, like anti-arrhythmia activity. Berberine exhibits a class-III antiarrhythmic activity and has been reported as useful in treating ventricular arrhythmia in clinic.

Since 1985, Ms. Meihua Xie (Research Fellow) from Shanghai Institute of Pharmaceutical Industry has designed and synthesized nearly 1,000 compounds that were derived from higenamine and berberine as the leading compounds via structural reconfiguration. These compounds were tested on antiarrhythmic pharmacodynamics, Ames toxicity, acute toxicity and pharmacokinetics, whereby 1-(3-methanesulfonamidobenzyl)-6-methoxy,7-benzyloxy-1,2,3,4-tetrahydroisoquinoline (referred to as "SIPI-409" herein below) of formula (II) was picked out as a candidate for a new antiarrhythmic drug for preclinical studies:

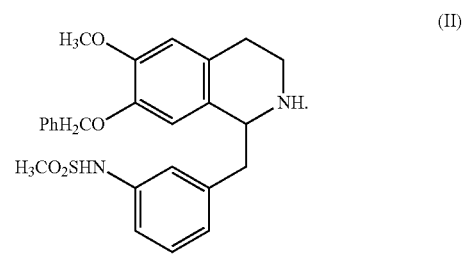

1-(3-methanesulfonamidobenzyl)-6-methoxy,7-benzyloxy-1,2,3,4-tetrahydroisoquinoline (SIPI-409) and its hydrochloride salt, as well as the preparation and uses thereof were described in Chinese Patent No. ZL200710181295.7.

However, further studies found that SIPI-409 and its hydrochloride salt were less soluble in water, as demonstrated by the solubility as low as 0.07 mg/mL (0.15 nmol/mL) and 0.51 mg/mL (1.05 nmol/mL), respectively. At the same time, preliminary pharmacokinetic studies have shown that $t_{1/2}$ of SIPI-409 hydrochloride injection was close to that of Sotalol, while oral administration of SIPI-409 hydrochloride gave a bioavailability (24%) far lower than Sotalol (70%) in SD rats. This can be explained by the excessively low solubility of the salt.

Therefore, there is a need for a salt derivative of the compound with improved water solubility, bioavailability and druggability.

SUMMARY

One object of the invention is to provide a salt derivative of SIPI-409 with improved solubility and preparation for same.

In the first aspect, the present invention provides a salt derivative of 1-(3-methanesulfonamidobenzyl)-6-methoxy,7-benzyloxy-1,2,3,4-tetrahydroisoquinoline having the structure of formula I:

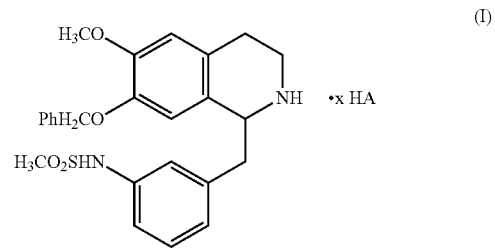

The salt derivative has a solubility of no less than 3.0 nmol/mL or 1.8 mg/mL in water.

In a preferred embodiment, HA is selected from the group consisting of sulfuric acid, phosphoric acid, nicotinic acid, oxalic acid, glycolic acid, benzenesulfonic acid and orotic acid; X is a value of ⅓, ½ or 1.

In another preferred embodiment, the salt derivative of 1-(3-methanesulfonamidobenzyl)-6-methoxy,7-benzyloxy-1,2,3,4-tetrahydroisoquinoline is in form of a crystal.

In another preferred embodiment, HA is sulfuric acid, and X is ½ or 1.

In another preferred embodiment, HA is oxalic acid, and X is ½ or 1.

In another preferred embodiment, when HA is sulfuric acid and X is 1, the crystal form of the crystal can be characterized by the following Bragg 2θ (Bragg 2-Theta) values as measured by X-ray powder diffraction (XRPD): 4.9±0.2°, 7.1±0.2°, 8.4±0.2°, 9.7±0.2°, 12.0±0.2°, 15.4±0.2°, 17.0±0.2°, 19.5°±0.2°, 20.3±0.2°, 20.9±0.2°, 21.6±0.2°, 22.8±0.2°, 23.6±0.2°, 24.6±0.2°, 25.4±0.2°, 26.0±0.2°, 30.8±0.2°; or by an endothermic peak at 130±5° C. in a DSC spectrum as measured by differential scanning calorimetry (DSC).

In another preferred embodiment, when X is 1 and HA is phosphoric acid, the crystal form of the crystal can be characterized by the following Bragg 2θ (Bragg 2-Theta) values as measured by X-ray powder diffraction (XRPD): 4.6±0.2°, 7.6±0.2°, 9.8±0.2°, 10.2±0.2°, 13.9±0.2°, 14.4±0.2°, 15.3±0.2°, 18.1±0.2°, 16.8±0.2°, 20.5±0.2°, 20.9±0.2°, 21.9±0.2°, 23.1±0.2°, 23.5±0.2°, 24.3±0.2°, 27.1±0.2°; or preferably, the crystal has the X-ray powder diffraction spectrum in FIG. 1.

In another preferred embodiment, when X is 1 and HA is phosphoric acid, the crystal exhibits an endothermic peak at 201±5° C. in a DSC spectrum as measured by differential scanning calorimetry (DSC); or preferably, the crystal has the DSC spectrum in FIG. 2.

In another preferred embodiment, when HA is nicotinic acid, the crystal form of the crystal can be characterized by the following Bragg 2θ (Bragg 2-Theta) values as measured by X-ray powder diffraction (XRPD): 5.0±0.2°, 5.9±0.2°, 7.2±0.2°, 8.2±0.2°, 10.9±0.2°, 12.2±0.2°, 13.4±0.2°, 14.4°±0.2°, 15.1±0.2°, 15.5±0.2°, 17.0±0.2°, 17.4±0.2°, 17.8±0.2°, 18.7±0.2°, 19.9±0.2°, 20.5±0.2°, 20.8±0.2°, 21.9±0.2°, 23.1±0.2°, 23.5±0.2°, 24.8±0.2°, 25.1±0.2°, 25.6±0.2°, 27.0±0.2°, 27.6±0.2°; or by an endothermic peak at 152±5° C. in a DSC spectrum as measured by differential scanning calorimetry (DSC).

In another preferred embodiment, when HA is oxalic acid and X is 1, the crystal form of the crystal can be characterized by the following Bragg 2θ (Bragg 2-Theta) values as measured by X-ray powder diffraction (XRPD): 3.4±0.2°, 4.6±0.2°, 5.5±0.2°, 7.8±0.2°, 9.2±0.2°, 10.2±0.2°, 10.8±0.2°, 11.9°±0.2°, 13.1±0.2°, 13.8±0.2°, 14.6±0.2°, 16.4±0.2°, 17.0±0.2°, 18.4±0.2°, 19.0±0.2°, 20.2±0.2°, 21.9±0.2°, 23.6±0.2°, 25.8±0.2°, 27.3±0.2°, 30.0±0.2°, 31.9±0.2°; or by an endothermic peak at 161±5° C. and a broad endothermic peak spanning 190~210° C. in a DSC spectrum as measured by differential scanning calorimetry (DSC).

In another preferred embodiment, when HA is glycolic acid, the crystal form of the crystal can be characterized by the following Bragg 2θ (Bragg 2-Theta) values as measured by X-ray powder diffraction (XRPD): 4.7±0.2°, 7.5±0.2°, 9.9±0.2°, 10.3±0.2°, 13.7±0.2°, 14.3±0.2°, 14.9±0.2°, 15.3°±0.2°, 16.1±0.2°, 16.9±0.2°, 17.6±0.2°, 18.1±0.2°, 18.9±0.2°, 19.3±0.2°, 20.4±0.2°, 20.8±0.2°, 21.8±0.2°, 22.5±0.2°, 22.9±0.2°, 24.3±0.2°, 24.9±0.2°, 25.3±0.2°, 25.9±0.2°, 27.7±0.2°; or by an endothermic peak at 187±5° C. in a DSC spectrum as measured by differential scanning calorimetry (DSC).

In another preferred embodiment, when HA is benzenesulfonic acid, the crystal form of the crystal can be characterized by the following Bragg 2θ (Bragg 2-Theta) values as measured by X-ray powder diffraction (XRPD): 6.1±0.2°, 6.8±0.2°, 8.2±0.2°, 8.8±0.2°, 11.5±0.2°, 12.7±0.2°, 14.4±0.2°, 15.0°±0.2°, 15.5±0.2°, 16.5±0.2°, 17.0±0.2°, 17.4±0.2°, 17.7±0.2°, 18.7±0.2°, 19.4±0.2°, 19.8±0.2°, 20.3±0.2°, 21.3±0.2°, 21.7±0.2°, 22.6±0.2°, 23.0±0.2°, 23.5±0.2°, 24.2±0.2°, 29.1±0.2°; or by an endothermic peak at 150±5° C. and a shoulder peak near 160° C. in a DSC spectrum as measured by differential scanning calorimetry (DSC).

In another preferred embodiment, when HA is orotic acid, the crystal form of the crystal can be characterized by the following Bragg 2θ (Bragg 2-Theta) values as measured by X-ray powder diffraction (XRPD): 5.8±0.2°, 8.7±0.2°, 9.9±0.2°, 11.2±0.2°, 12.5±0.2°, 13.9±0.2°, 14.1±0.2°, 15.2±0.2°, 16.2±0.2°, 16.2±0.2°, 17.0±0.2°, 17.4±0.2°, 17.8±0.2°, 18.7±0.2°, 19.0±0.2°, 20.4±0.2°, 21.9±0.2°, 23.5±0.2°, 24.0±0.2°, 24.9±0.2°, 25.9±0.2°, 27.6±0.2°, 29.5±0.2°, 31.0±0.2°, 31.4±0.2°; or by an endothermic peak at 138±5° C. in a DSC spectrum as measured by differential scanning calorimetry (DSC).

In the second aspect, the present invention provides a method for preparing the provided salt derivative of 1-(3-methanesulfonamidobenzyl)-6-methoxy,7-benzyloxy-1,2,3,4-tetrahydroisoquinoline according to the present invention, comprising reacting 1-(3-methanesulfonamidobenzyl)-6-methoxy,7-benzyloxy-1,2,3,4-tetrahydroisoquinoline with the acid HA to form the salt derivative.

In another preferred embodiment, the method comprises reacting 1-(3-methanesulfonamidobenzyl)-6-methoxy,7-benzyloxy-1,2,3,4-tetrahydroisoquinoline provided according to the present disclosure as described above with the acid in an organic solvent to form the salt derivative.

In another preferred embodiment, the method comprises, when HA is nicotinic acid, oxalic acid, glycolic acid, benzenesulfonic acid or orotic acid, dissolving 1-(3-methanesulfonamidobenzyl)-6-methoxy,7-benzyloxy-1,2,3,4-tetrahydroisoquinoline in an organic solvent, adding the acid, and then cooling to crystallize to give the product.

In another preferred embodiment, the method comprises, when HA is sulfuric acid or phosphoric acid, dissolving 1-(3-methanesulfonamidobenzyl)-6-methoxy,7-benzyloxy-1,2,3,4-tetrahydroisoquinoline in an organic solvent, adding the acid in a organic solvent, and then cooling to crystallize to give the product.

In another preferred embodiment, the method further comprises washing and drying the obtained crystal or precipitate.

In another preferred embodiment, the reaction is conducted at a temperature of 0-80° C.

In another preferred embodiment, the organic solvent is methanol, ethanol, isopropanol, acetone, 2-butanone, methyl acetate, isopropyl acetate, methyl tertbutyl ether, acetonitrile or toluene.

In another preferred embodiment, when HA is phosphoric acid, the temperature of reaction is 10-60° C.; more preferably 40° C.

In the third aspect, the present invention provides a pharmaceutical composition consisting of an effective amount of the provided salt derivative of 1-(3-methanesulfonamidobenzyl)-6-methoxy,7-benzyloxy-1,2,3,4-tetrahydroisoquinoline according to the present invention and one or more pharmaceutically acceptable auxiliary agent(s).

In the fourth aspect, the present invention provides use of the provided salt derivative of 1-(3-methanesulfonamidobenzyl)-6-methoxy,7-benzyloxy-1,2,3,4-tetrahydroisoquinoline according to the present invention in preparing an antiarrhythmic medicament.

Thereby, the present invention provides a salt derivative of the compound with improved solubility in water and thus also improved bioavailability and druggability.

B: XRPD spectra of the starting material SIPI-409 and the product of its reaction with succinic acid;

C: XRPD spectra of the starting material SIPI-409 and the product of its reaction with glycolic acid;

D: XRPD spectra of the starting material SIPI-409 and the product of its reaction with oxalic acid;

E: XRPD spectra of the starting material SIPI-409 and the product of its reaction with orotic acid;

F: XRPD spectra of the starting material SIPI-409 and the product of its reaction with fumaric acid;

G: XRPD spectra of the starting material SIPI-409 and the product of its reaction with tartaric acid;

H: XRPD spectra of the starting material SIPI-409 and the product of its reaction with ethionic acid;

I: XRPD spectra of the starting material SIPI-409 and the product of its reaction with malic acid;

J: XRPD spectra of the starting material SIPI-409 and the product of its reaction with hydrobromic acid;

K: XRPD spectra of the starting material SIPI-409 and the product of its reaction with phosphoric acid;

L: XRPD spectra of the starting material SIPI-409 and the product of its reaction with nicotinic acid;

M: XRPD spectra of the starting material SIPI-409 and the product of its reaction with sulfuric acid; and N: XRPD spectra of the starting material SIPI-409 and the product of its reaction with benzenesulfonic acid.

Figure 16:
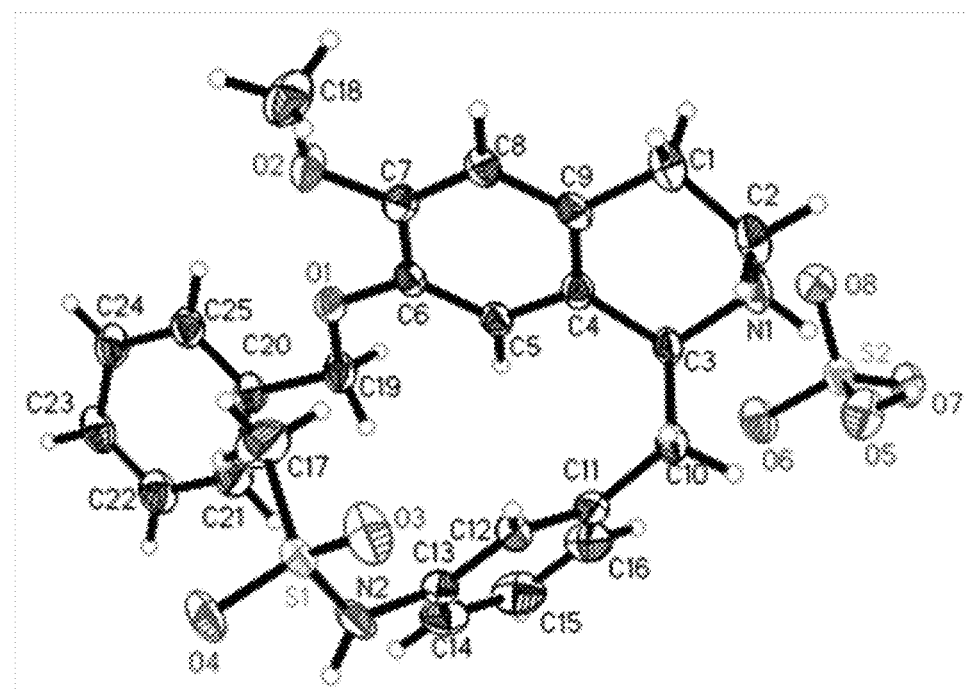

FIG. 16 is a projection of the monocrystal stereostructure of SIPI-409 sulfate crystal.

Figure 17:
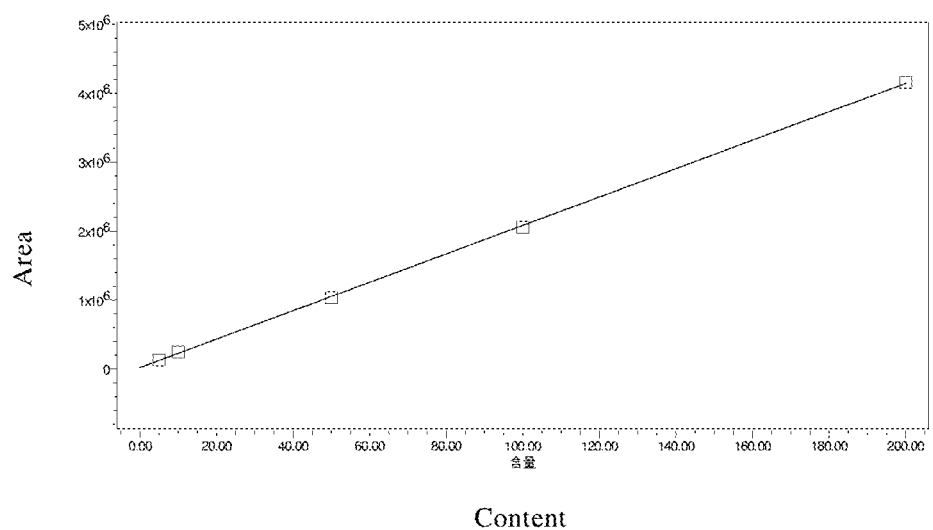
Figure 18A:
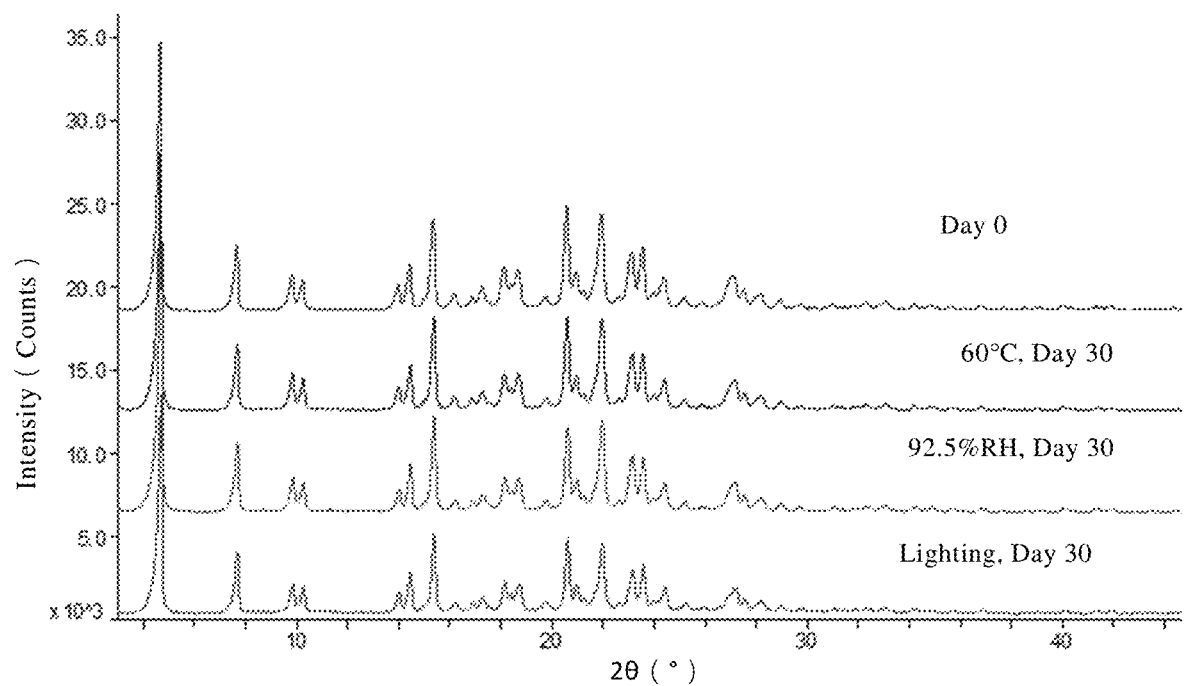
Figure 18B:
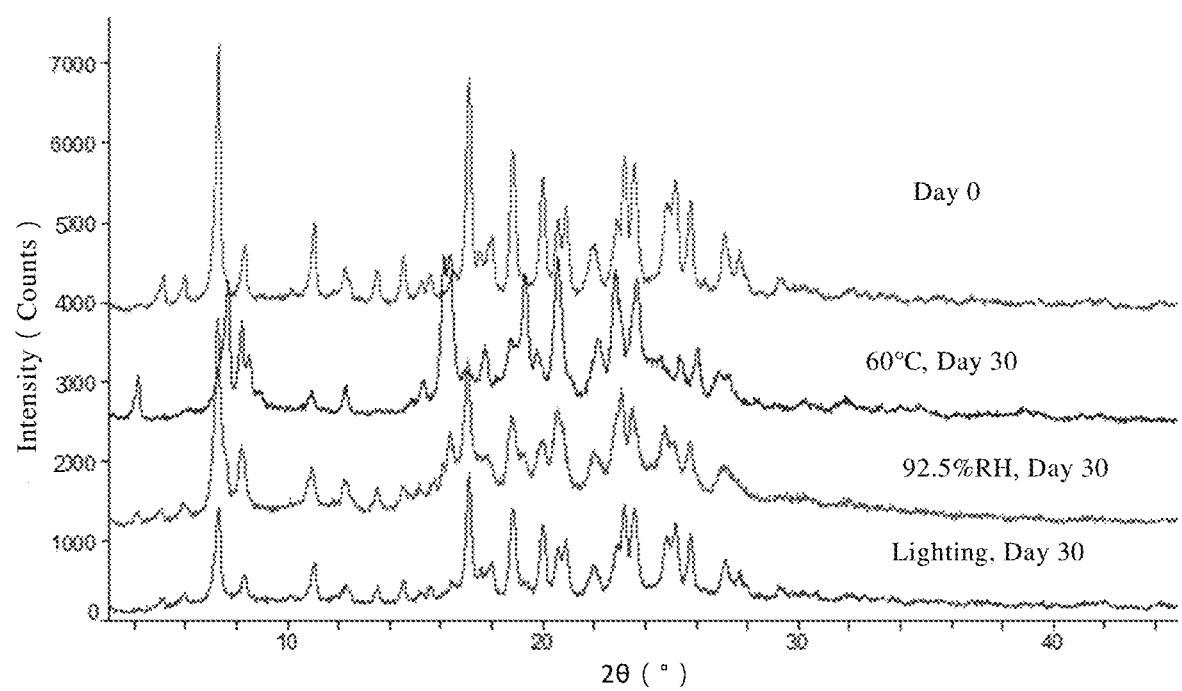
Figure 18C:
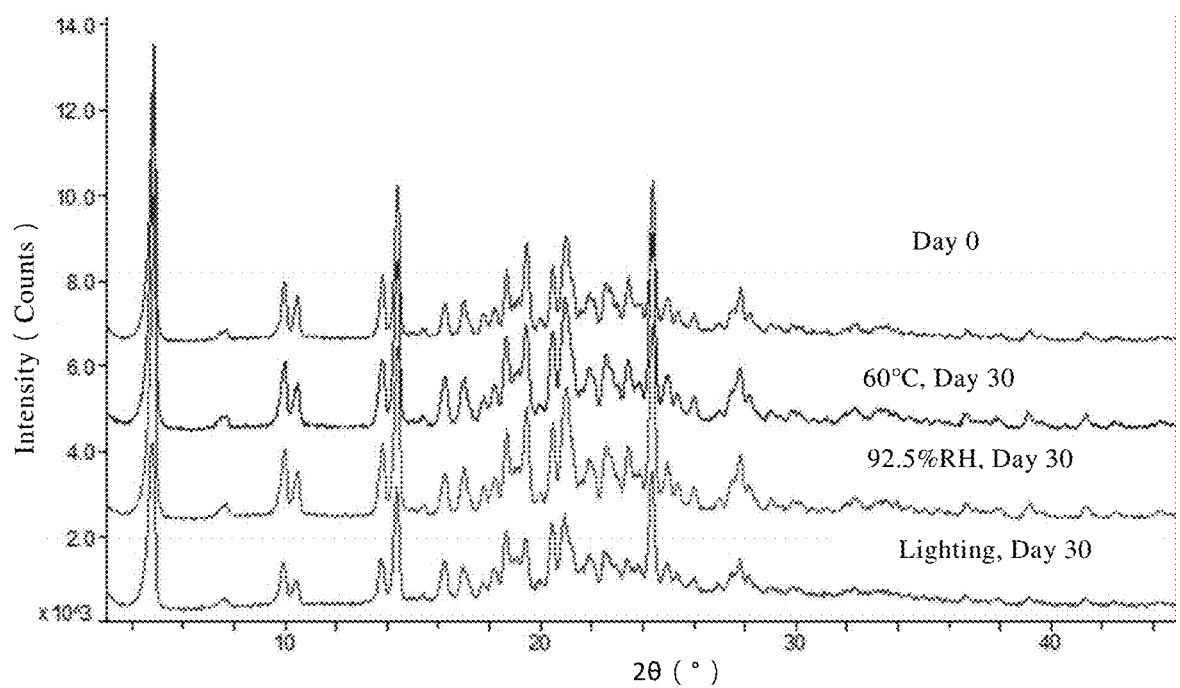
Figure 18D:
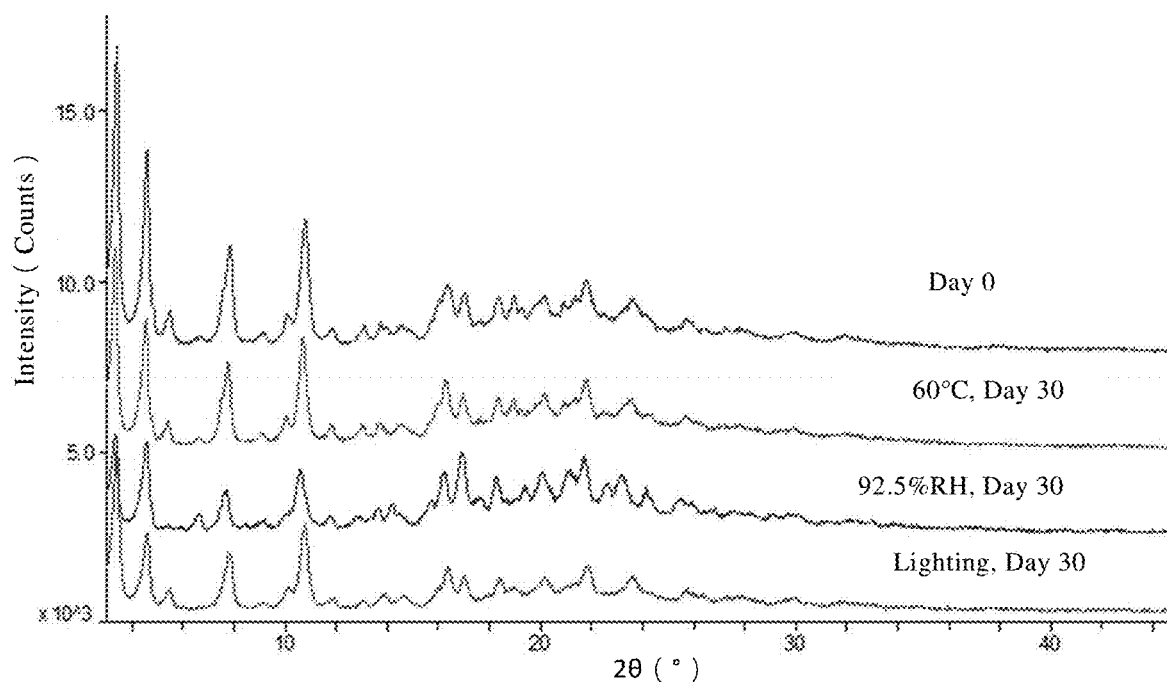
Figure 18E:
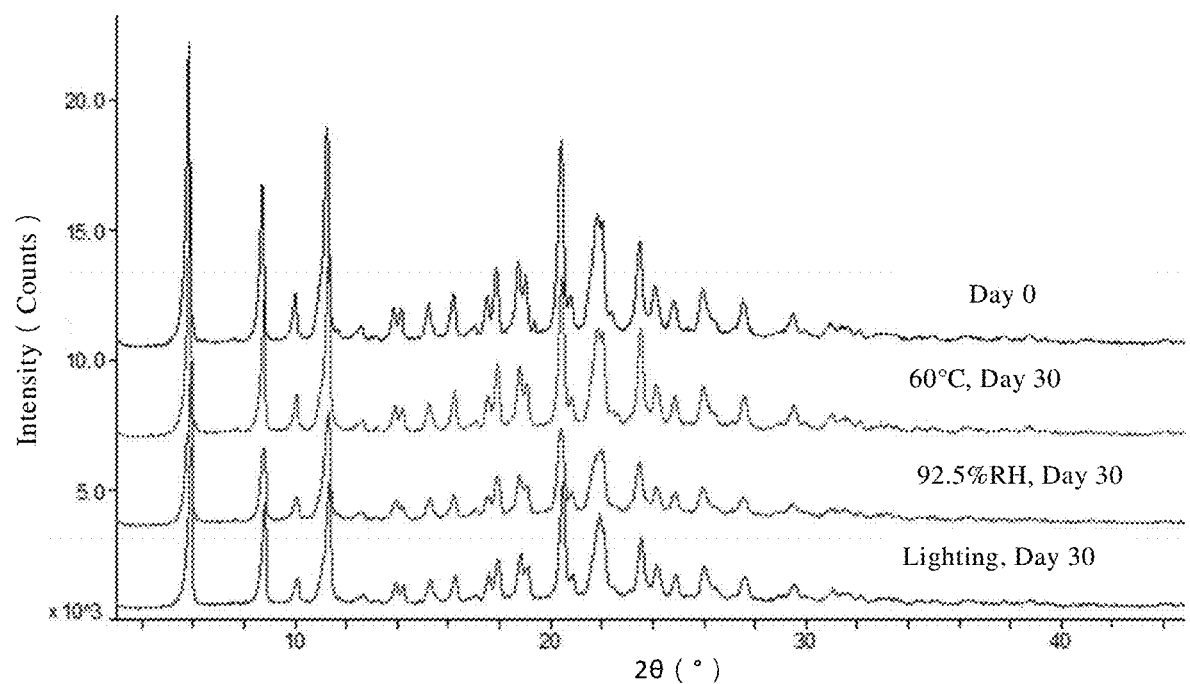
Figure 18F:
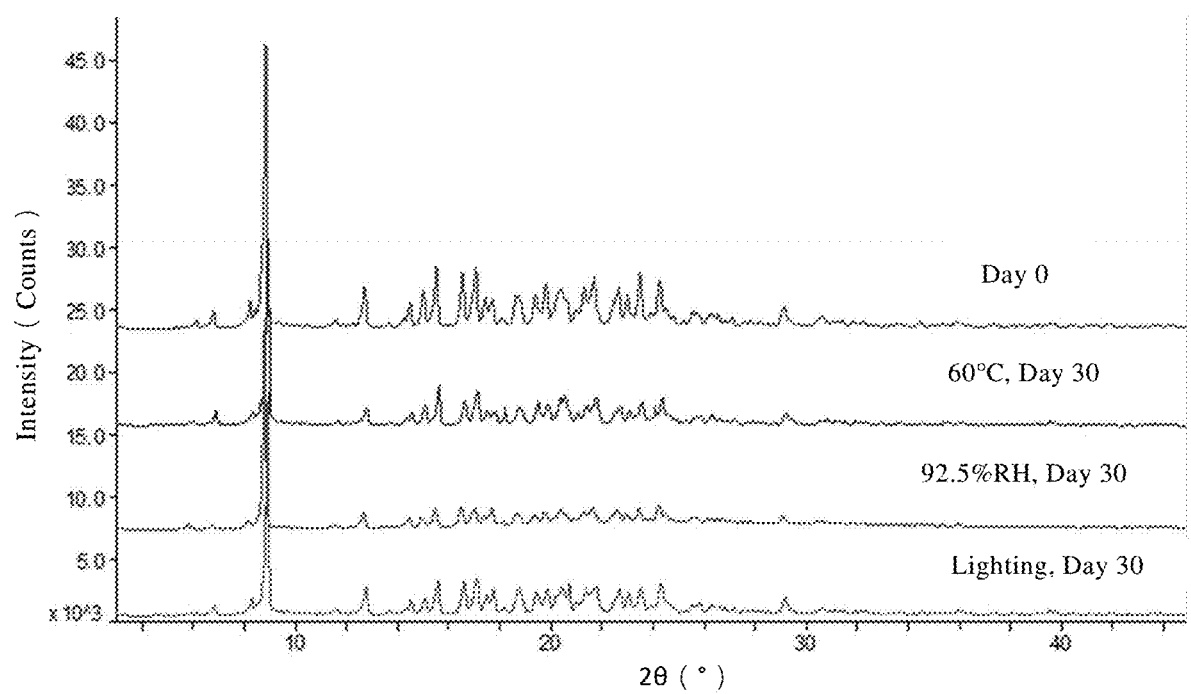
Figure 18G:
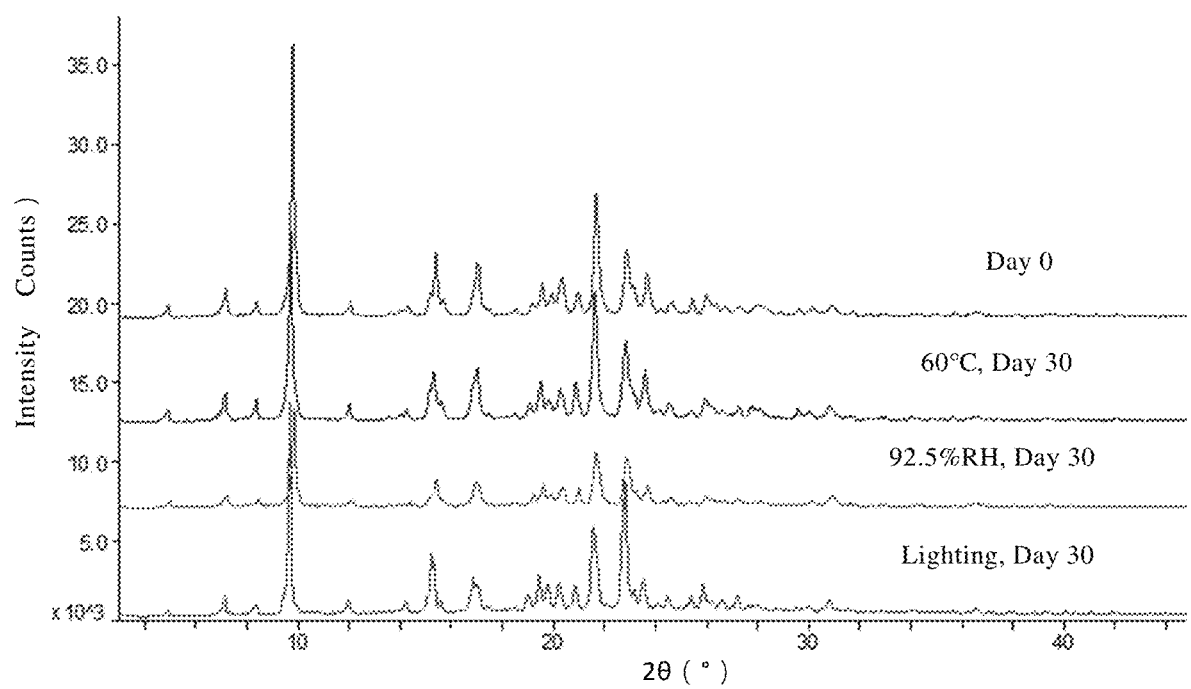

FIG. 17 is the standard curve of solubility obtained with the SIPI-409 standard. The value of R is 0.999932.

FIG. 18 exhibits the XRPD spectra obtained for each of the salt derivatives of SIPI-409 in investigations on crystalline stability, wherein, A: XRPD spectra of SIPI-409 phosphate in the crystalline stability investigations;

B: XRPD spectra of SIPI-409 nicotinate in the crystalline stability investigations;

C: XRPD spectra of SIPI-409 glycolate in the crystalline stability investigations;

D: XRPD spectra of SIPI-409 oxalate in the crystalline stability investigations;

E: XRPD spectra of SIPI-409 orotate in the crystalline stability investigations;

F: XRPD spectra of SIPI-409 benzenesulfonate in the crystalline stability investigations; and G: XRPD spectra of SIPI-409 sulfate in the crystalline stability investigations.

DETAILED DESCRIPTION

The present inventors find, trough extensive and intensive investigation, that the salt derivative of 1-(3-methanesulfonamidobenzyl)-6-methoxy,7-benzyloxy-1,2,3,4-tetrahydroisoquinoline according to formula I exhibits significantly improved solubility in water, compared to the existing SIPI-409 and its hydrochloride form. Further, pharmacokinetics show that the salt derivatives of SIPI-409 according to the present invention exhibit significantly improved bioavailability, compared to the existing SIPI-409 hydrochloride. For example, in the case of the phosphate, the bioavailability can be increased by 329%, compared to the existing SIPI-409 hydrochloride.

The present invention provides a salt derivative of the compound SIPI-409 according to formula (I):

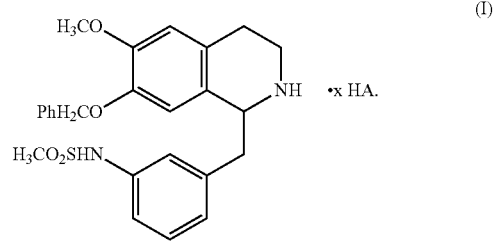

Therein, the acid used to form the salt with SIPI-40 409 can be any of the organic or inorganic acids as commonly known in the art, such as one selected from the list below in Table 1.

TABLE 1

| Type | Acids | | | |
|---|---|---|---|---|
| Acids of type I | Hydrochloric acid | Hexanedioic acid | Hippuric acid | Isoleucine |
| | Sulfuric acid | Citric acid | Decanoic acid | Threonine |
| | Phosphoric acid | Ferulic acid | Lauric acid | Lysine |
| | Acetic acid | Phenylpropionic acid | Palmitic acid | Alanine |
| | Glycolic acid | Phenylbutyric acid | Stearic acid | Cystine |
| | Lactic acid | Valproic acid | Succinic acid | Arginine |
| | L-Lactic acid | Iodic acid | L-(−)-Malic acid | Tyrosine |
| | L-Aspartic acid | Methylsulfuric acid | L-(+)-Tartaric acid | Proline |
| | Gluconic acid | Valeric acid | Maleic acid | Glutamic acid |
| | D-Glucuronic acid | Valine | Fumaric acid | Hydrobromic acid |
| | Ascorbic acid | Leucine | Glutaric acid | Sebacic acid |
| | D-glutamic acid | L-Glutamic acid | Mucic acid | — |
| Acids type II | Methane sulfonic acid | Benzoic Acid | 2-Ketoglutaric acid | Toluene-4-sulfonic acid, monohydrate |
| | Hydroxyethanesulphonic acid | Octanoic acid | 1-hydroxy-2-naphthoic acid | 2-naphthalenesulfonic acid (hydrate) |
| | Propionic acid | Alginic acid | (+)-camphoric acid | 1,5-naphthalene disulfonic acid |
| | Iso-butyric acid | Nicotinic acid | Pamoic acid | 2,5-dihydroxybenzoic acid |
| | Orotic acid | Lactobionic acid | Malonic acid | Cyclohexane sulfanilic acid |
| | L-Pyroglutamic acid | Oleic acid | Oxalic acid dihydrate | 1,2-ethionic acid |
| | Benzenesulfonic acid | Anhydrous oxalic acid | — | — |
| Acids of type III | Nitric acid | Formic acid | P-aminosalicylic acid | D-camphor-10-sulfonic acid |
| | Mandelic acid | Salicylic acid | Undecylenic acid | 4-acetamidobenzoic acid |
| | Dichloroacetic acid | Cinnamic acid | — | — |

Products of a primary screening on salt type were subjected to an XRPD measurement. XRPD spectra of the reaction products between SIPI-409 and the acids such as hydrochloric acid, succinic acid, fumaric acid, L-tartaric acid, ethionic acid, glycolic acid, orotic acid, DL-malic acid, hydrobromic acid, oxalic acid, phosphoric acid, nicotinic acid, sulfuric acid and benzenesulfonic acid were compared with the XRPD spectrum of the starting material SIPI-409 in FIG. 15. As shown, the XRPD spectra of the fourteen (14) reaction products are significantly different in terms of diffraction pattern, position of the angles and diffraction intensity, as compared to SIPI-409. Thereby, it can be preliminarily concluded that all the fourteen (14) acids form salts with SIPI-409. Preferably, phosphoric acid, sulfuric acid, nicotinic acid, oxalic acid, glycolic acid, benzenesulfonic acid or orotic acid is used to form the salt with SIPI-409. And more preferably, sulfuric acid, phosphoric acid, nicotinic acid or oxalic acid is used.

Figure 1:
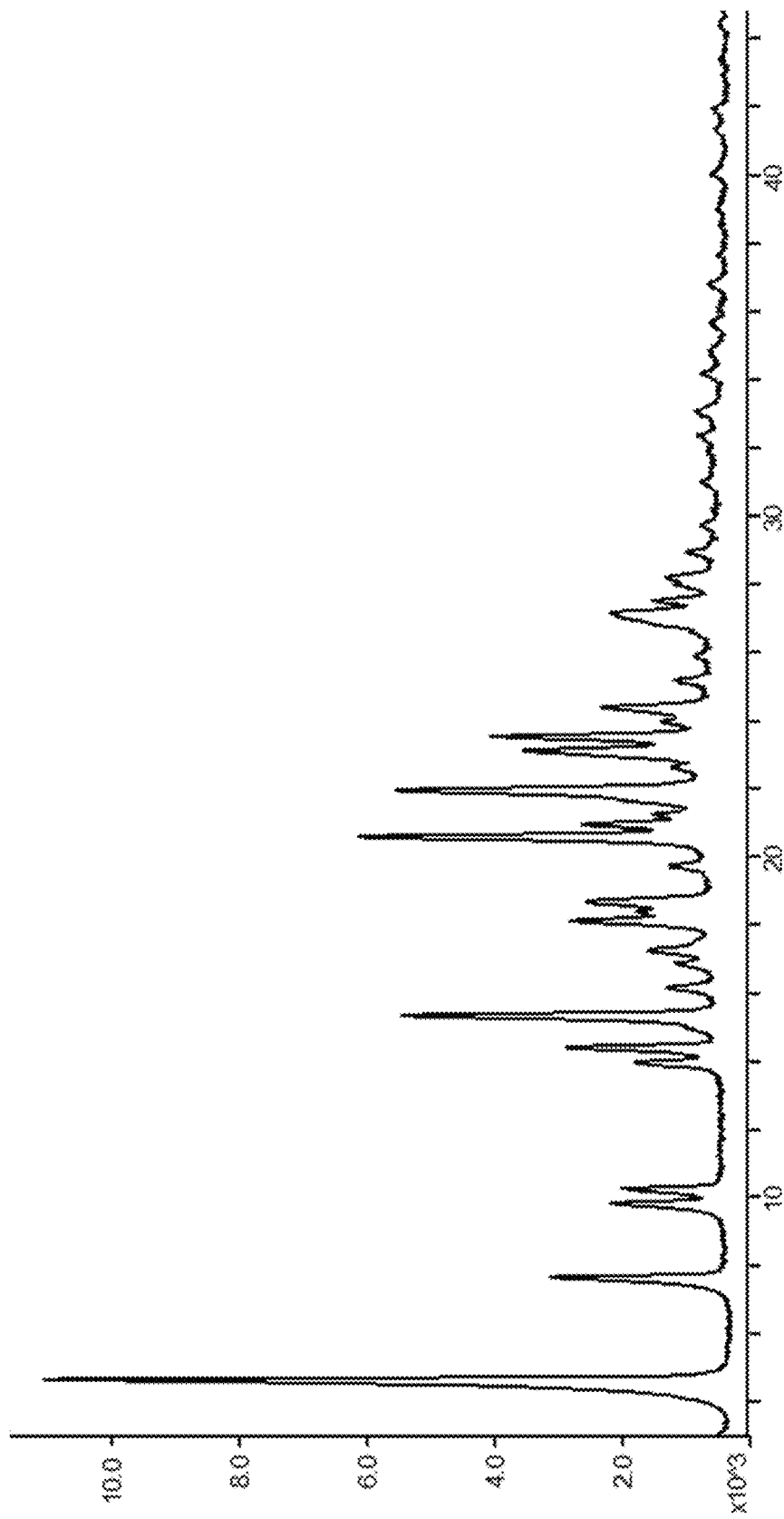
FIG. 1 is an XRPD spectrum of SIPI-409 phosphate crystal measured using a Cu target radiation source, wherein the horizontal axis indicates positions (2θ value) and the vertical axis intensities of the diffraction peaks.

The provided SIPI-409 phosphate crystal according to the present invention comprises SIPI-409 and phosphoric acid at a ratio being 1:1, 2:1 or 3:1; wherein, when the ratio of SIPI-409 to phosphoric acid is 1:1, the resultant crystal, as measured via powder X-ray diffraction using a Cu target radiation source, has the following characteristic 2θ peaks: 4.6±0.2°, 7.6±0.2°, 9.8±0.2°, 10.2±0.2°, 13.9±0.2°, 14.4±0.2°, 15.3±0.2°, 18.1±0.2°, 16.8±0.2°, 20.5±0.2°, 20.9±0.2°, 21.9±0.2°, 23.1±0.2°, 23.5±0.2°, 24.3±0.2°, 27.1±0.2°; or more preferably, has the XRPD spectrum in FIG. 1.

Figure 2:
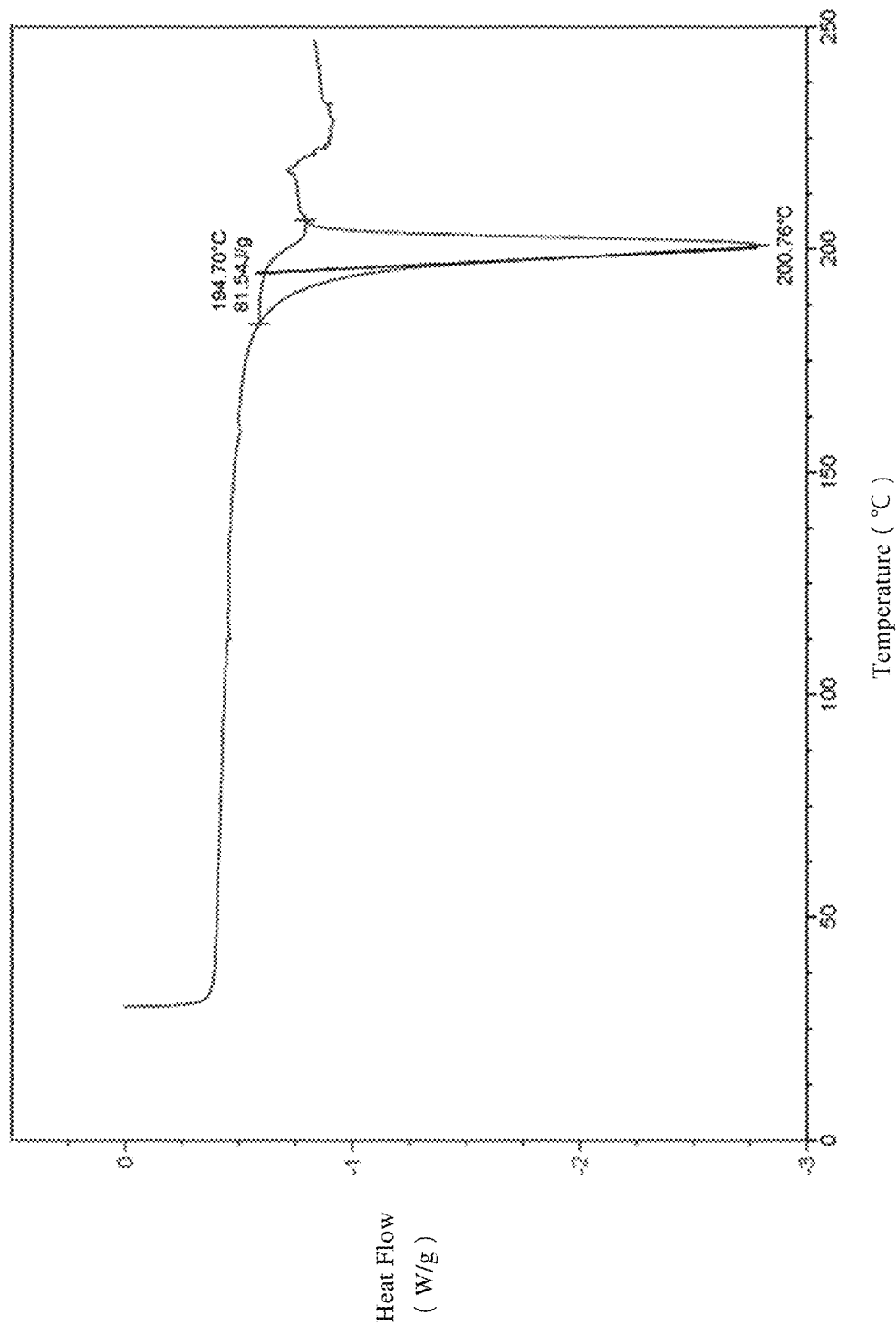
FIG. 2 is a DSC spectrum of SIPI-409 phosphate crystal, wherein the endothermic peak is expressed downward.

The said SIPI-409 phosphate crystal, as measured by differential scanning calorimetry, is observed with an endothermic peak at 201±5° C. in the DSC spectrum at a temperature rate of 10° C./min, or preferably has the DSC spectrum in FIG. 2.

Figure 3:
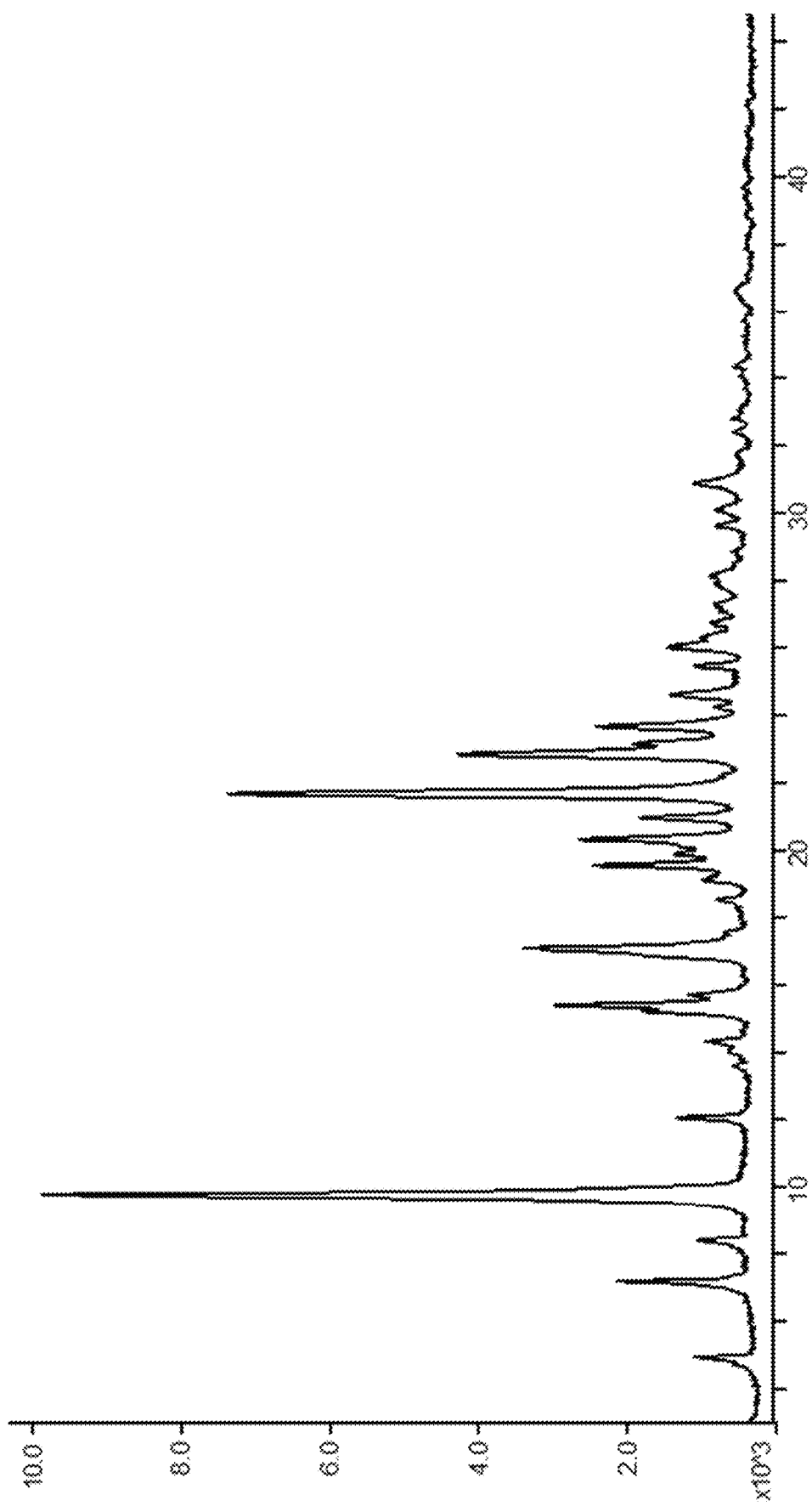
FIG. 3 is an XRPD spectrum of SIPI-409 sulfate crystal measured using a Cu target radiation source, wherein the horizontal axis indicates positions (2θ value) and the vertical axis intensities of the diffraction peaks.

The provided SIPI-409 sulfate crystal according to the present invention comprises SIPI-409 and sulfuric acid at a ratio of 1:1 or 2:1; wherein, when the ratio of SIPI-409 to sulfuric acid is 1:1, the resultant crystal, as measured via powder X-ray diffraction using a Cu target radiation source, has the following characteristic 2θ peaks: 4.9±0.2°, 7.1±0.2°, 8.4±0.2°, 9.7±0.2°, 12.0±0.2°, 15.4±0.2°, 17.0±0.2°, 19.5°±0.2°, 20.3±0.2°, 20.9±0.2°, 21.6±0.2°, 22.8±0.2°, 23.6±0.2°, 24.6±0.2°, 25.4±0.2°, 26.0±0.2°, 30.8±0.2°; or preferably, has the XRPD spectrum of FIG. 3.

Figure 4:
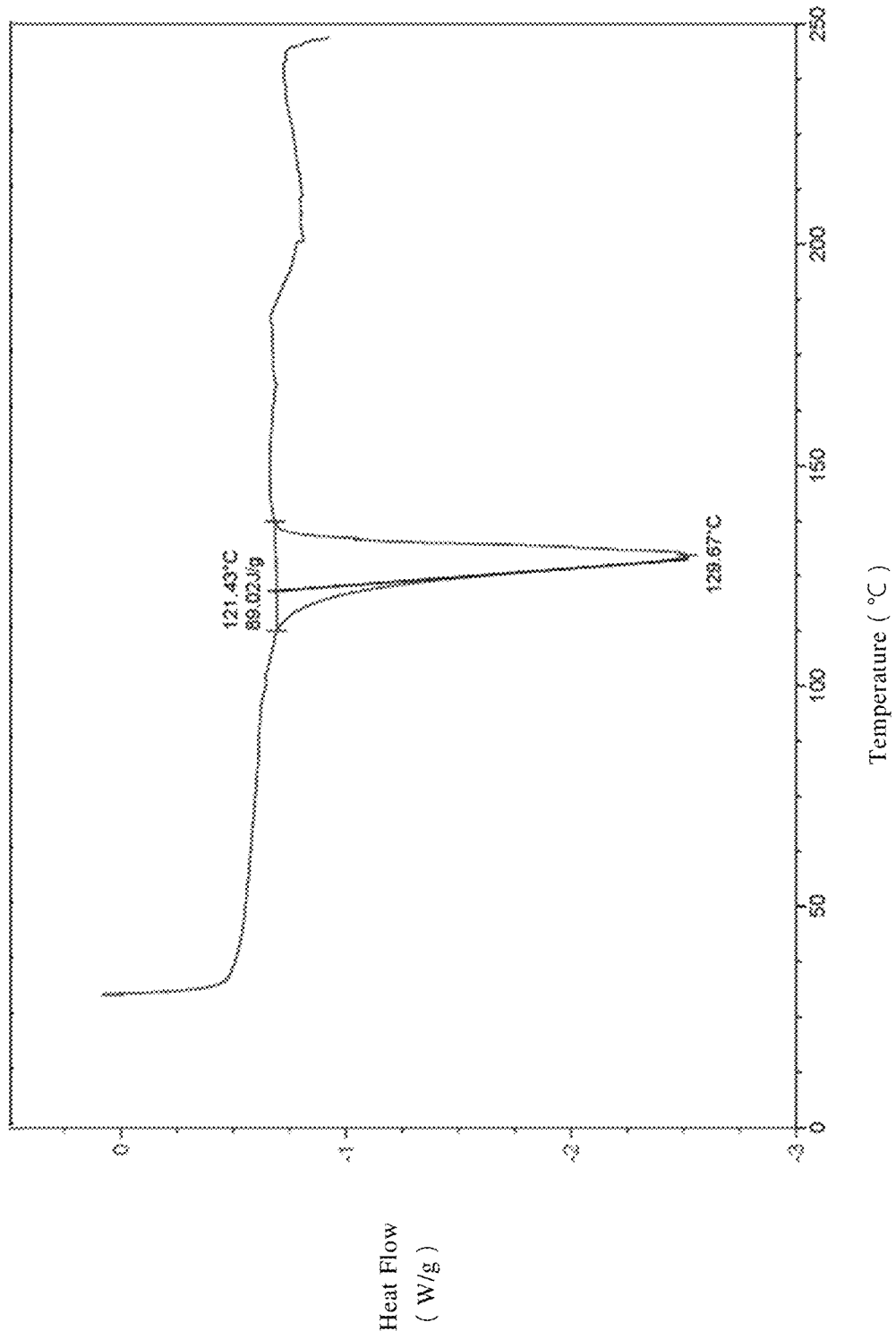
FIG. 4 is a DSC spectrum of SIPI-409 sulfate crystal, wherein the endothermic peak is expressed downward.

The said SIPI-409 sulfate crystal, as measured by differential scanning calorimetry (DSC), is observed with an endothermic peak at 130±5° C. in the DSC spectrum at a temperature rate of 10° C./min, or preferably has the DSC spectrum in FIG. 4.

Monocrystal of said SIPI-409 sulfate crystal ($C_{25}H_{28}N_2O_4 \cdot H_2SO_4$) is in the form of colorless transparent cakes and has a crystalline density of 1.361 g/cm$^3$, a space group of P-1, cell parameters of a=10.292 Å, b=11.499 Å, c=12.982 Å, α=94.86°, β=106.70° and γ=110.95°, cell volume (V)=1343.85 Å$^3$ and the number of asymmetric units in cell (Z)=2. (FIG. 16)

Figure 5:
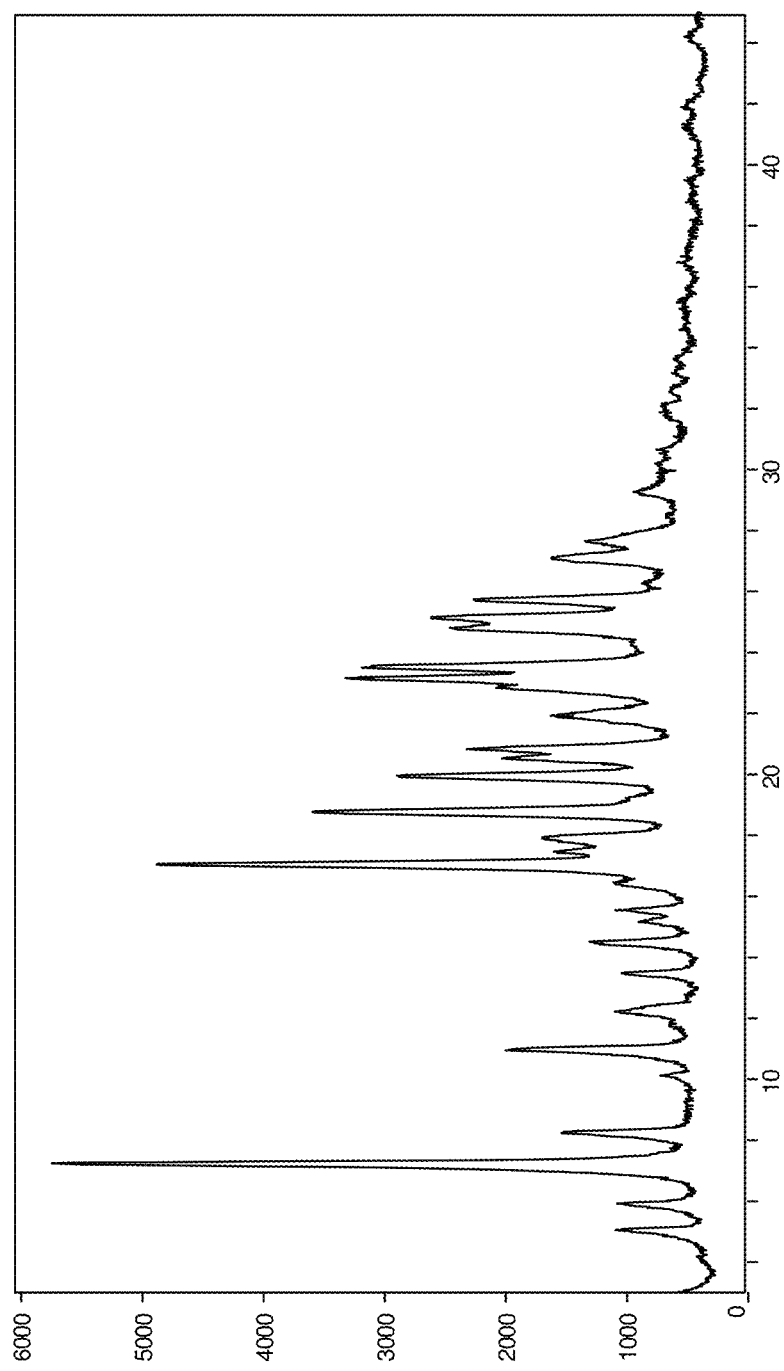
FIG. 5 is an XRPD spectrum of SIPI-409 nicotinate crystal measured using a Cu target radiation source, wherein the horizontal axis indicates positions (2θ value) and the vertical axis intensities of the diffraction peaks.

The provided SIPI-409 nicotinate crystal according to the present invention, as measured via powder X-ray diffraction using a Cu target radiation source, has the following characteristic 2θ peaks: 5.0±0.2°, 5.9±0.2°, 7.2±0.2°, 8.2±0.2°, 10.9±0.2°, 12.2±0.2°, 13.4±0.2°, 14.4°±0.2°, 15.1±0.2°, 15.5±0.2°, 17.0±0.2°, 17.4±0.2°, 17.8±0.2°, 18.7±0.2°, 19.9±0.2°, 20.5±0.2°, 20.8±0.2°, 21.9±0.2°, 23.1±0.2°, 23.5±0.2°, 24.8±0.2°, 25.1±0.2°, 25.6±0.2°, 27.0±0.2°, 27.6±0.2°; or preferably, has the XRPD spectrum of FIG. 5.

Figure 6:
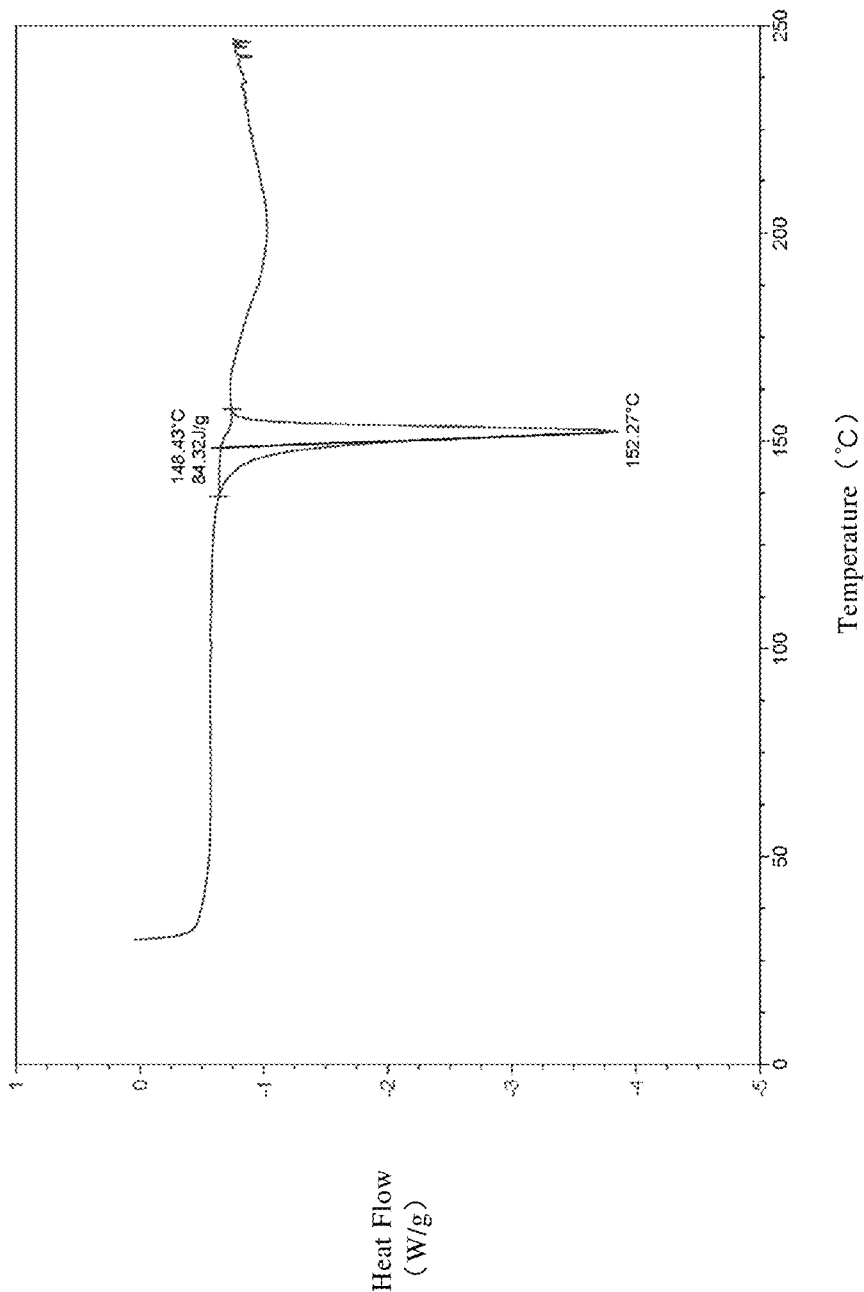
FIG. 6 is a DSC spectrum of SIPI-409 nicotinate crystal, wherein the endothermic peak is expressed downward.

The provided SIPI-409 nicotinate crystale according to the present invention, as measured by differential scanning calorimetry (DSC), is observed with an endothermic peak at 152±5° C. in the DSC spectrum at a temperature rate of 10° C./min or preferably has the DSC spectrum in FIG. 6.

Figure 7:
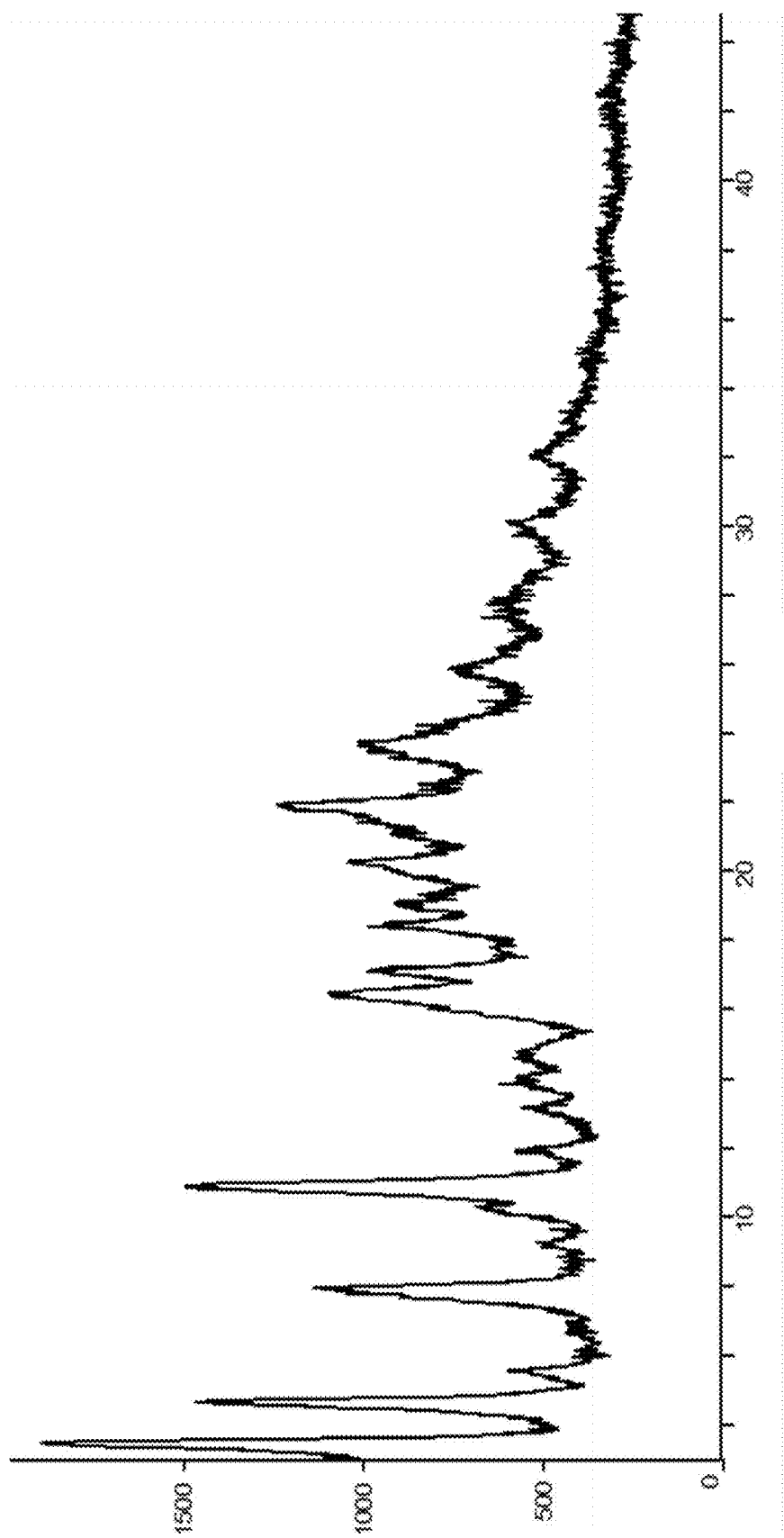
FIG. 7 is an XRPD spectrum of SIPI-409 oxalate crystal measured using a Cu target radiation source, wherein the horizontal axis indicates positions (2θ value) and the vertical axis intensities of the diffraction peaks.

The provided SIPI-409 oxalate crystal according to the present invention comprises SIPI-409 and oxalic acid at a ratio being 1:1 or 2:1; wherein when the ratio of SIPI-409 to oxalic acid is 1:1, the resultant crystal, as measured via powder X-ray diffraction using a Cu target radiation source, has the following characteristic 2θ peaks: 3.4±0.2°, 4.6±0.2°, 5.5±0.2°, 7.8±0.2°, 9.2±0.2°, 10.2±0.2°, 10.8±0.2°, 11.9°±0.2°, 13.1±0.2°, 13.8±0.2°, 14.6±0.2°, 16.4±0.2°, 17.0±0.2°, 18.4±0.2°, 19.0±0.2°, 20.2±0.2°, 21.9±0.2°, 23.6±0.2°, 25.8±0.2°, 27.3±0.2°, 30.0±0.2°, 31.9±0.2°; or preferably, has the XRPD spectrum of FIG. 7.

Figure 8:
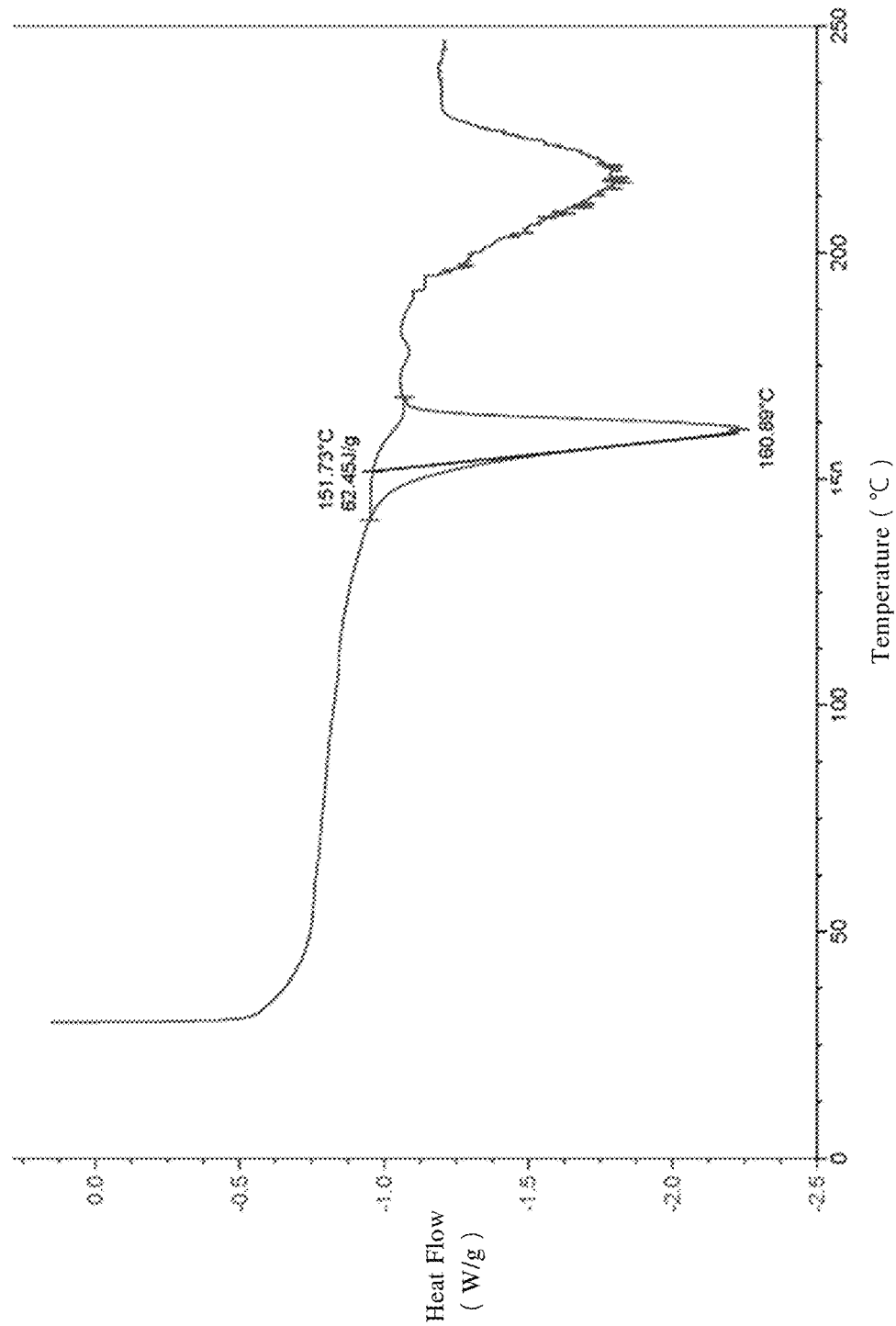
FIG. 8 is a DSC spectrum of SIPI-409 oxalate crystal, wherein the endothermic peak is expressed downward.

The said SIPI-409 oxalate crystal, as measured by differential scanning calorimetry (DSC), is observed with an endothermic peak at 161±5° C. and a broad endothermic peak spanning 190~210° C. in the DSC spectrum at a temperature rate of 10° C./min or preferably has the DSC spectrum in FIG. 8

Figure 9:
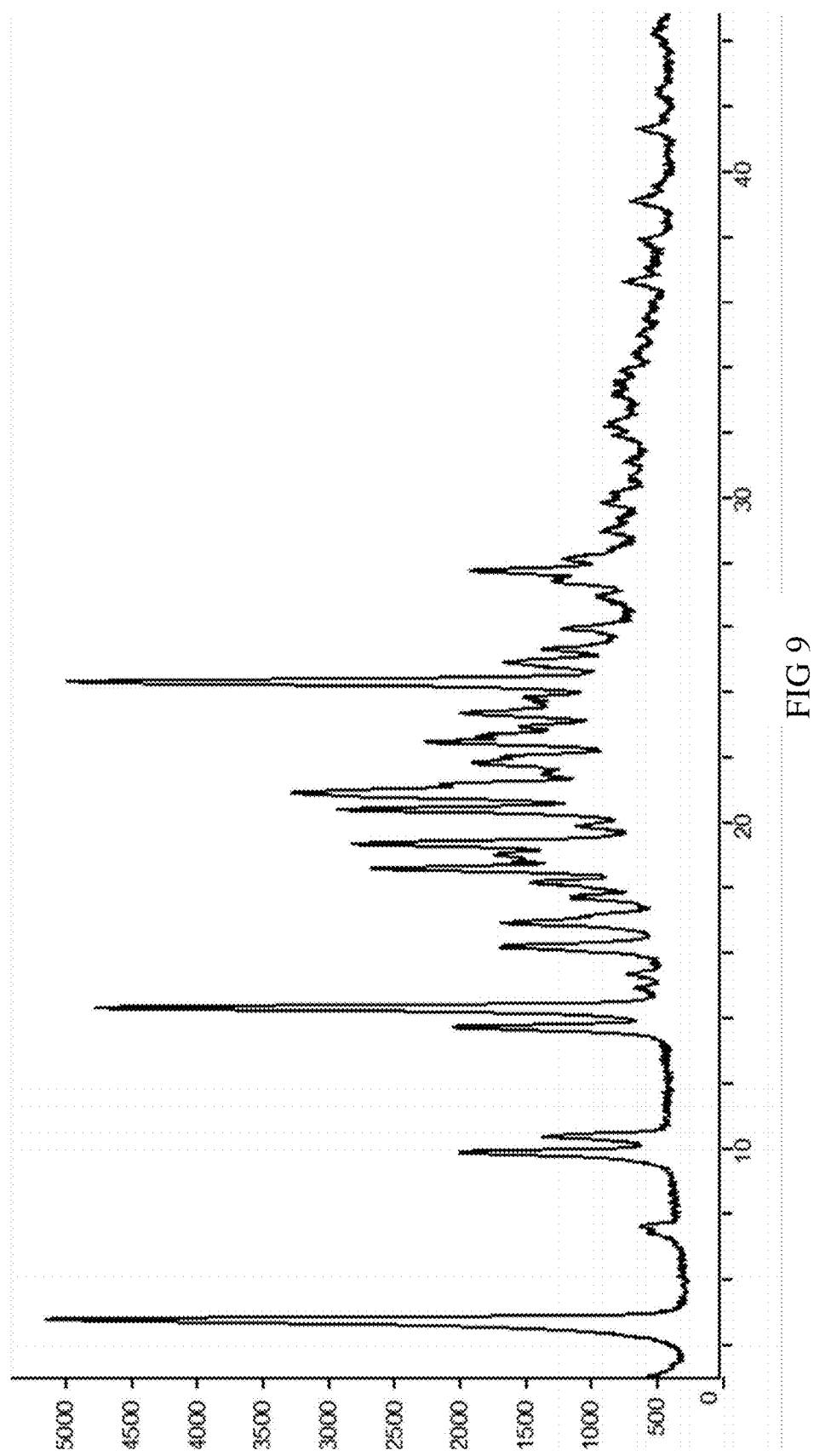
FIG. 9 is an XRPD spectrum of SIPI-409 glycolate crystal measured using a Cu target radiation source, wherein the horizontal axis indicates positions (2θ value) and the vertical axis intensities of the diffraction peaks.

The provided SIPI-409 glycolate crystal according to the present invention, as measured via powder X-ray diffraction using a Cu target radiation source, has the following characteristic 2θ peaks: 4.7±0.2°, 7.5±0.2°, 9.9±0.2°, 10.3±0.2°, 13.7±0.2°, 14.3±0.2°, 14.9±0.2°, 15.3°±0.2°, 16.1±0.2°, 16.9±0.2°, 17.6±0.2°, 18.1±0.2°, 18.9±0.2°, 19.3±0.2°, 20.4±0.2°, 20.8±0.2°, 21.8±0.2°, 22.5±0.2°, 22.9±0.2°, 24.3±0.2°, 24.9±0.2°, 25.3±0.2°, 25.9±0.2°, 27.7±0.2°; or preferably, has the XRPD spectrum of FIG. 9.

Figure 10:
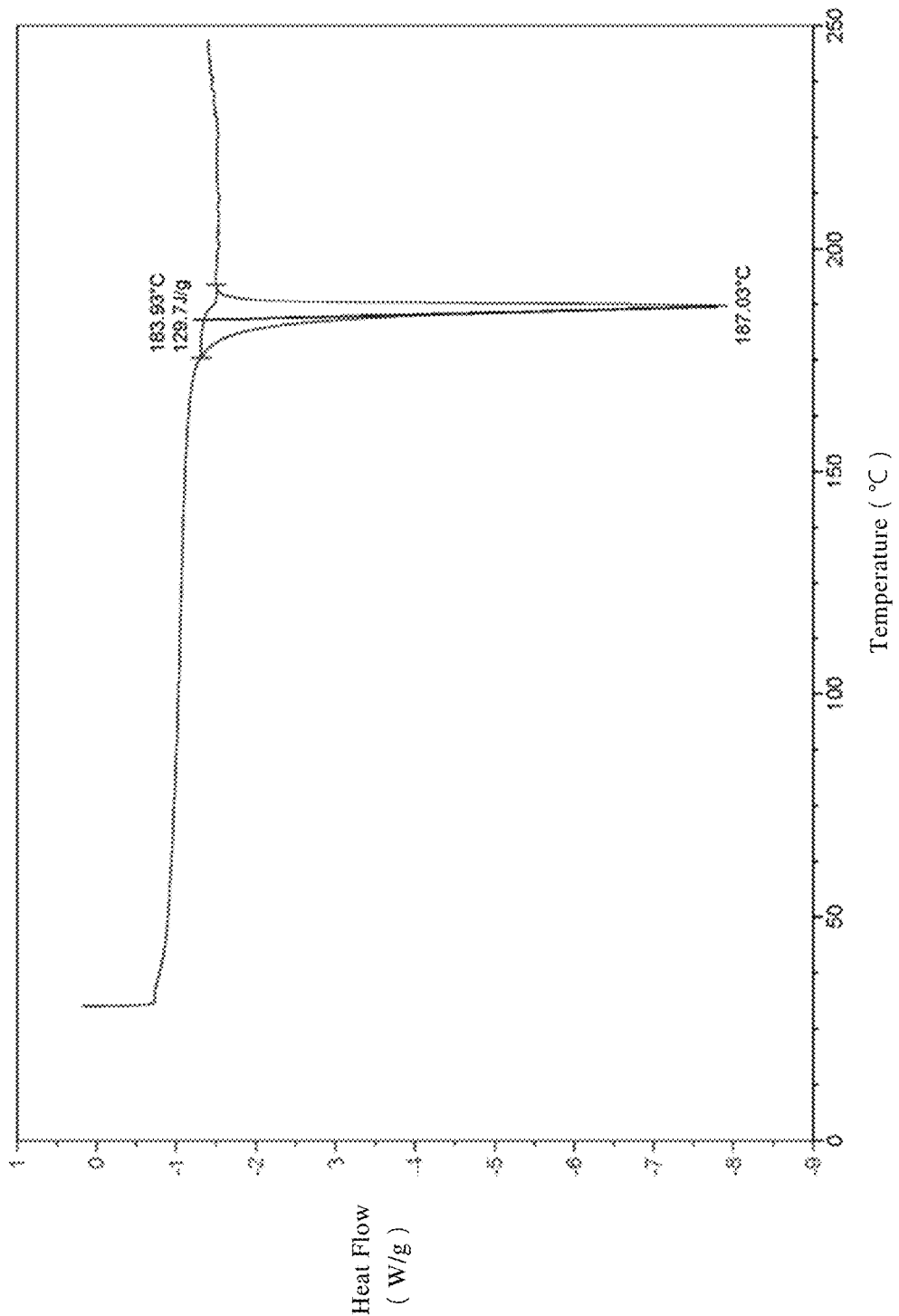
FIG. 10 is a DSC spectrum of SIPI-409 glycolate crystal, wherein the endothermic peak is expressed downward.

The provided SIPI-409 glycolate crystal according to the present invention, as measured by differential scanning calorimetry (DSC), is observed with an endothermic peak at 187±5° C. in the DSC spectrum at a temperature rate of 10° C./min or preferably has the DSC spectrum in FIG. 10.

Figure 11:
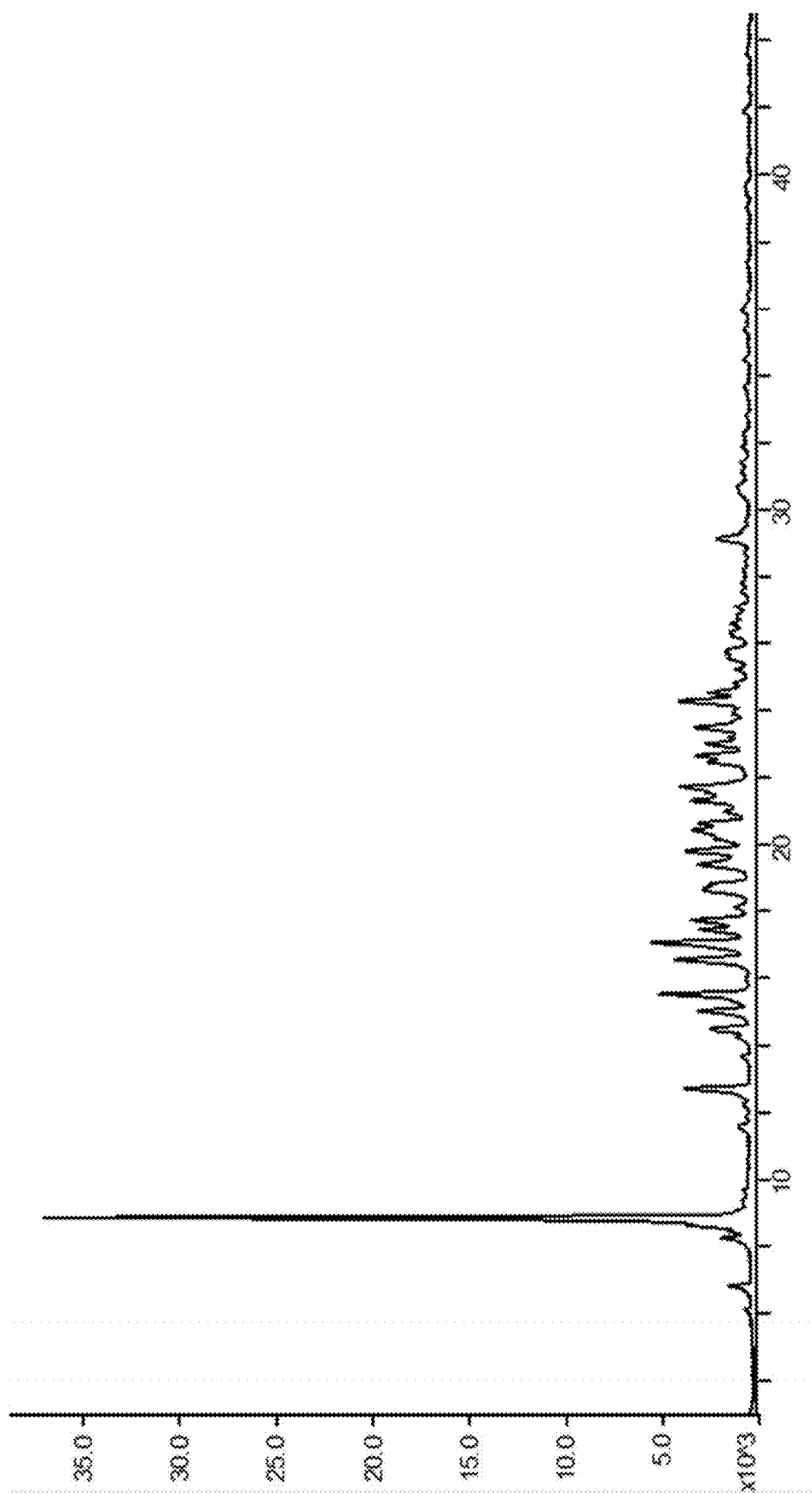
FIG. 11 is an XRPD spectrum of SIPI-409 benzenesulfonate crystal measured using a Cu target radiation source, wherein the horizontal axis indicates positions (2θ value) and the vertical axis intensities of the diffraction peaks.

The provided SIPI-409 benzenesulfonate crystal according to the present invention, as measured via powder X-ray diffraction using a Cu target radiation source, has the following characteristic 2θ peaks: 6.1±0.2°, 6.8±0.2°, 8.2±0.2°, 8.8±0.2°, 11.5±0.2°, 12.7±0.2°, 14.4±0.2°, 15.0°±0.2°, 15.5±0.2°, 16.5±0.2°, 17.0±0.2°, 17.4±0.2°, 17.7±0.2°, 18.7±0.2°, 19.4±0.2°, 19.8±0.2°, 20.3±0.2°, 21.3±0.2°, 21.7±0.2°, 22.6±0.2°, 23.0±0.2°, 23.5±0.2°, 24.2±0.2°, 29.1±0.2°; or preferably, has the XRPD spectrum of FIG. 11.

Figure 12:
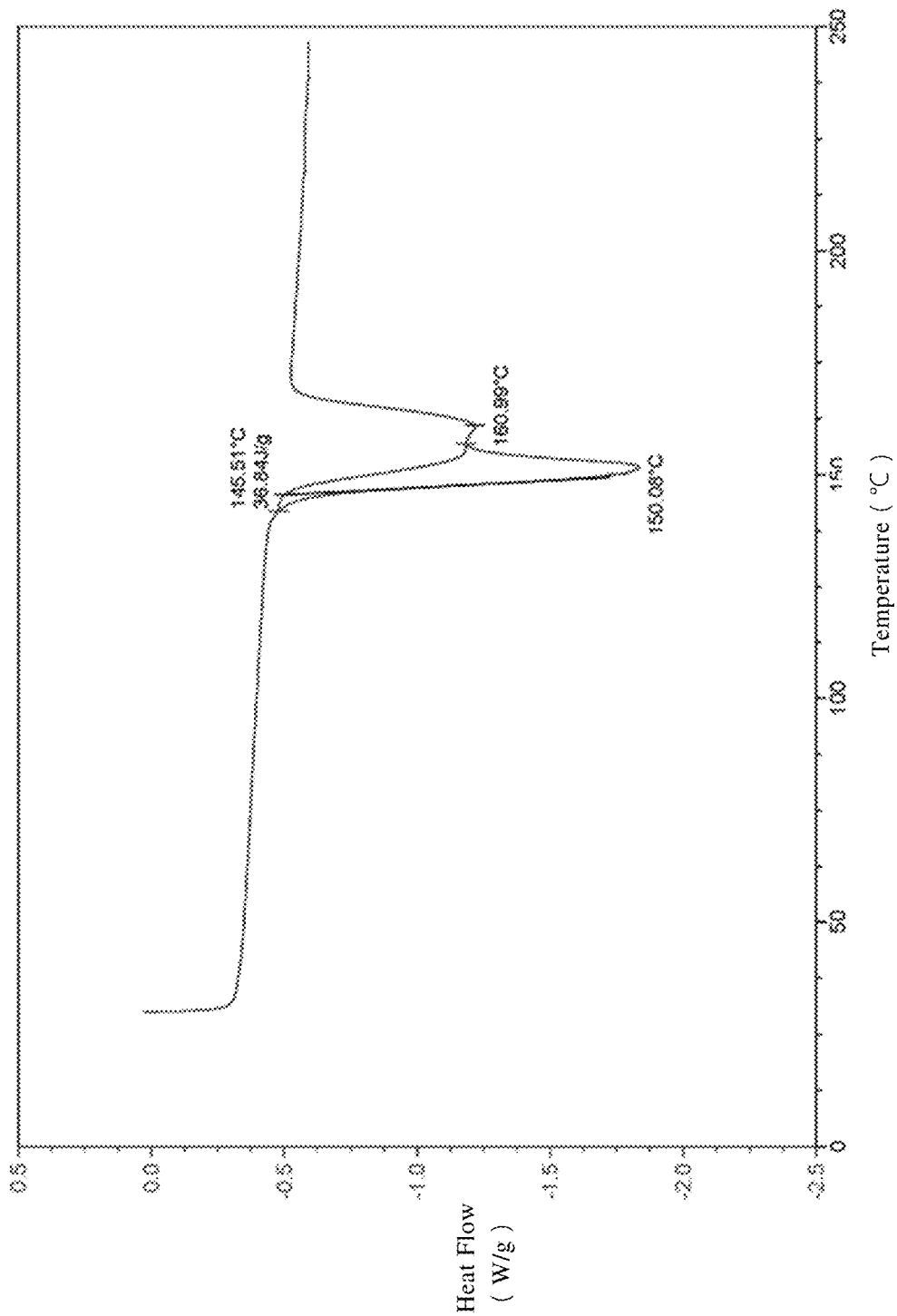
FIG. 12 is a DSC spectrum of SIPI-409 benzenesulfonate crystal, wherein the endothermic peak is expressed downward.

The provided SIPI-409 benzenesulfonate crystal according to the present invention, as measured by differential scanning calorimetry (DSC), is observed with an endothermic peak at 150±5° C. and a shoulder peak near 160° C. in the DSC spectrum at a temperature rate of 10° C./min or preferably has the DSC spectrum in FIG. 12.

Figure 13:
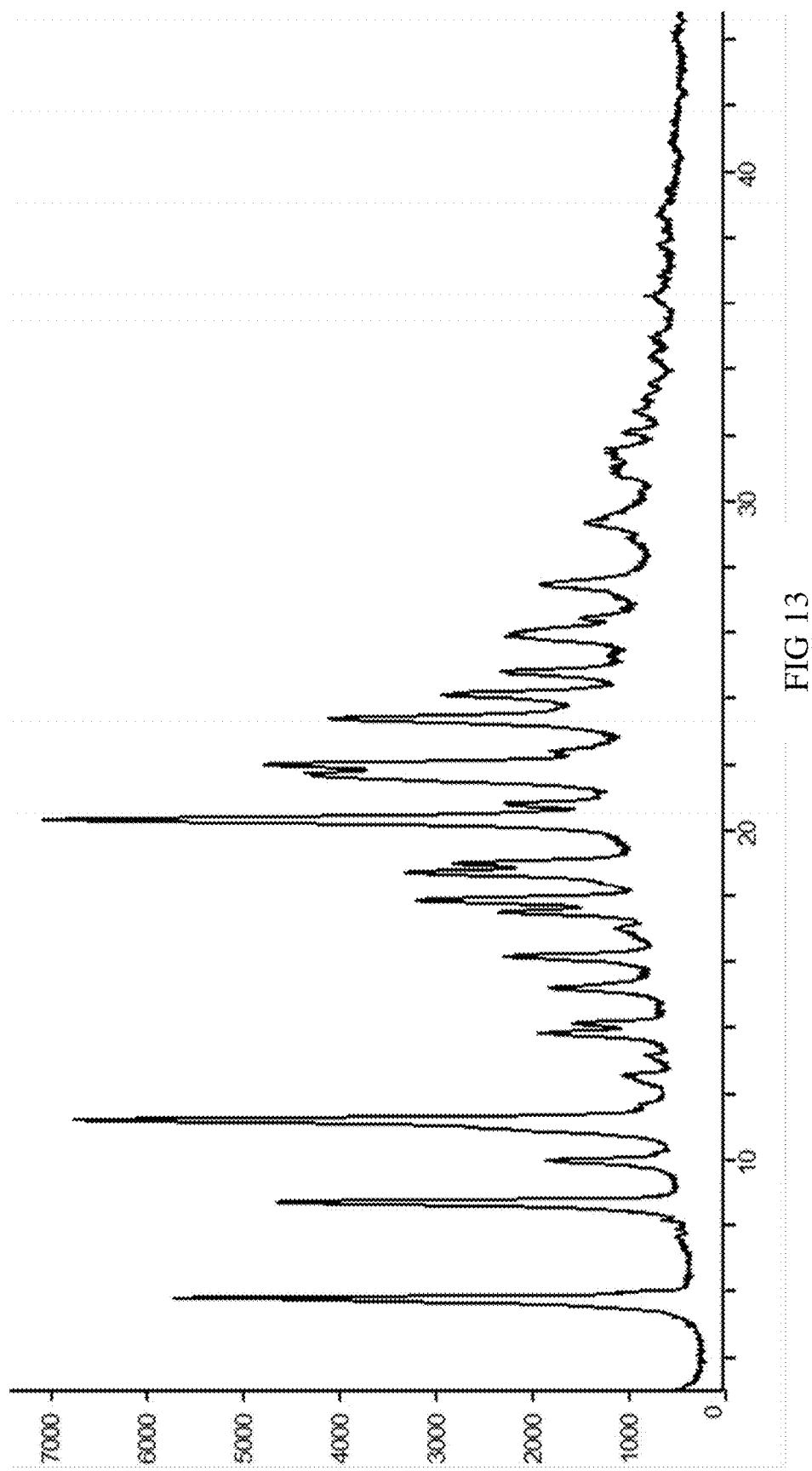
FIG. 13 is an XRPD spectrum of SIPI-409 orotate crystal measured using a Cu target radiation source, wherein the horizontal axis indicates positions (2θ value) and the vertical axis intensities of the diffraction peaks.

The provided SIPI-409 orotate crystal according to the present invention, as measured via powder X-ray diffraction using a Cu target radiation source, has the following characteristic 2θ peaks: 5.8±0.2°, 8.7±0.2°, 9.9±0.2°, 11.2±0.2°, 12.5±0.2°, 13.9±0.2°, 14.1±0.2°, 15.2°±0.2°, 16.2±0.2°, 17.0±0.2°, 17.4±0.2°, 17.8±0.2°, 18.7±0.2°, 19.0±0.2°, 20.4±0.2°, 21.9±0.2°, 23.5±0.2°, 24.0±0.2°, 24.9±0.2°, 25.9±0.2°, 27.6±0.2°, 29.5±0.2°, 31.0±0.2°, 31.4±0.2°; or preferably, has the XRPD spectrum of FIG. 13.

Figure 14:
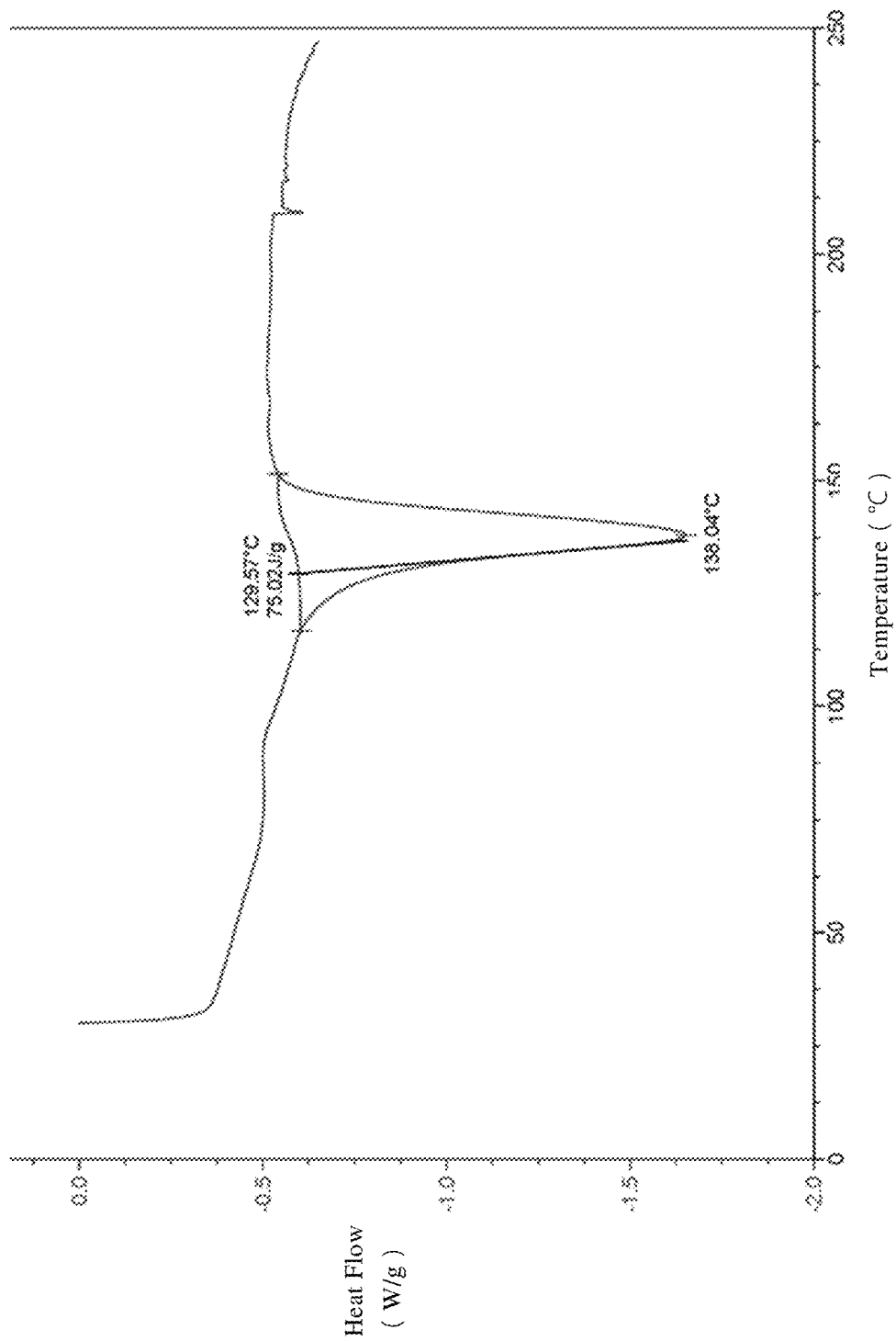
FIG. 14 is a DSC spectrum of SIPI-409 orotate crystal, wherein the endothermic peak is expressed downward.
Figure 15A:
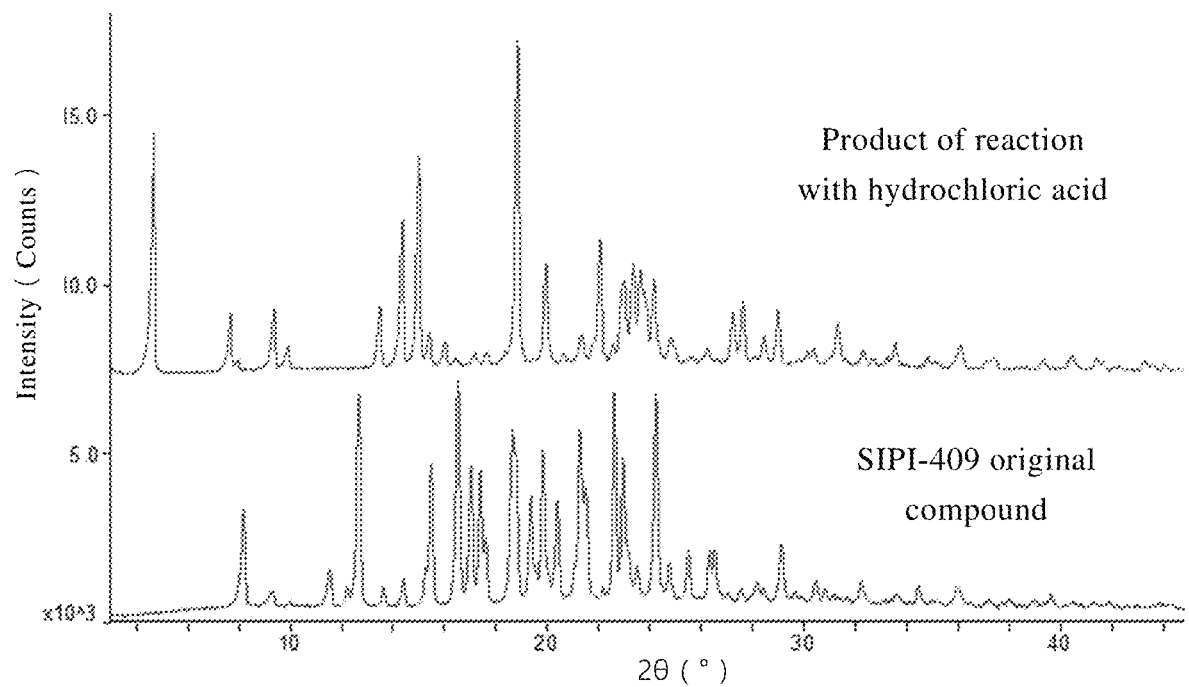
FIG. 15 is a comparison of XRPD spectra between the products of the reactions between SIPI-409 and the 14 acids and the starting material SIPI-409; wherein, A: XRPD spectra of the starting material SIPI-409 and the product of its reaction with hydrochloric acid.
Figure 15B:
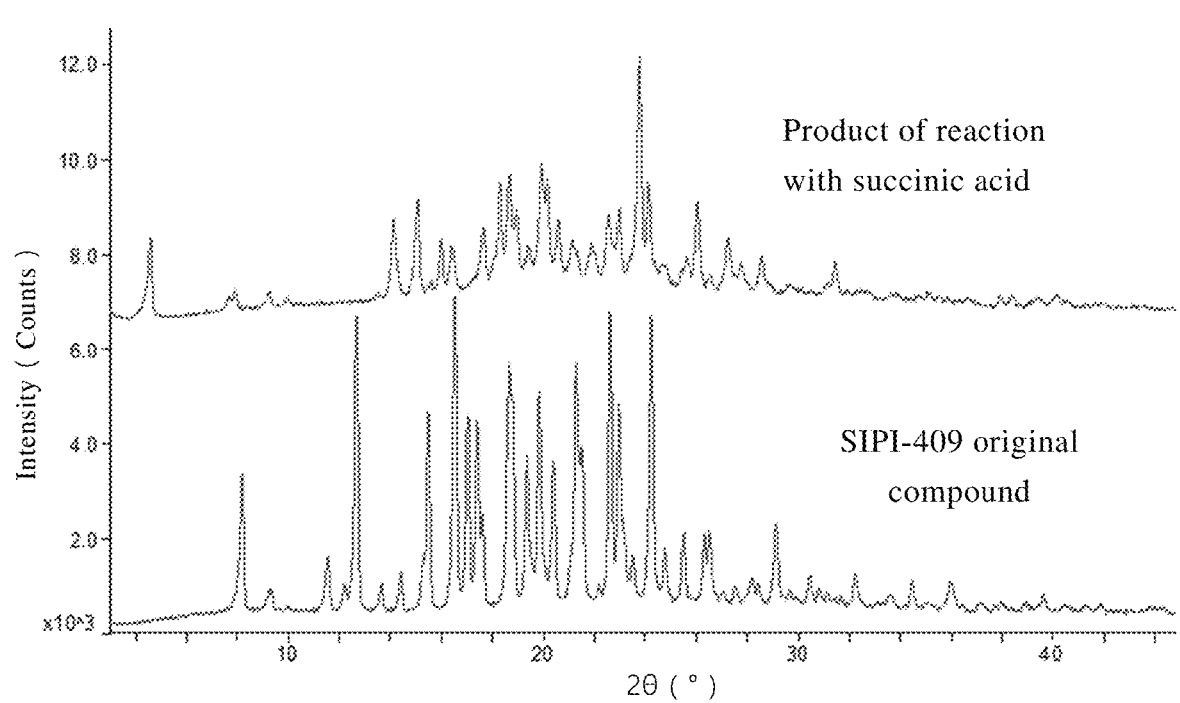
Figure 15C:
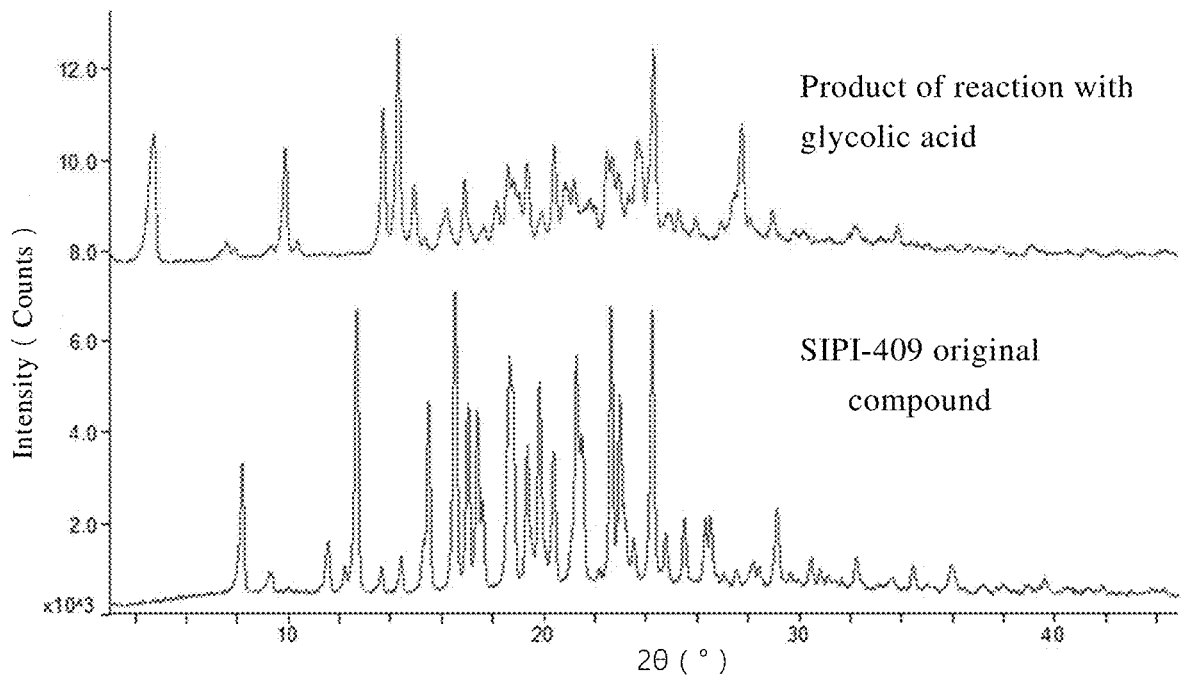
Figure 15D:
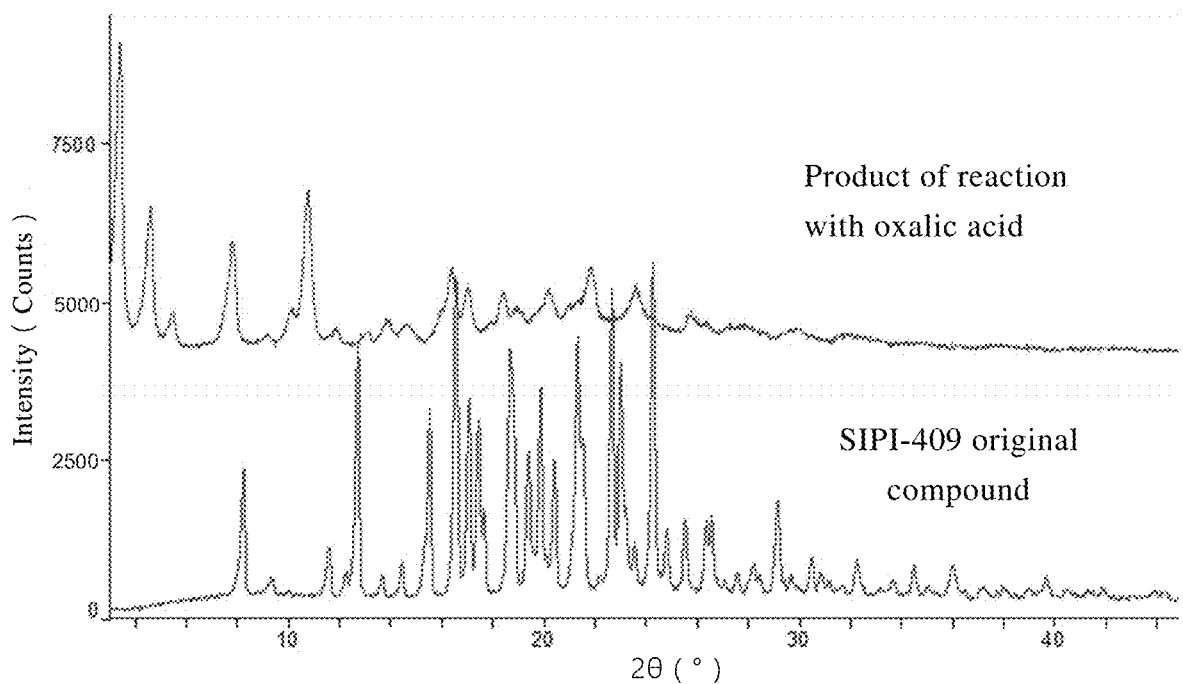
Figure 15E:
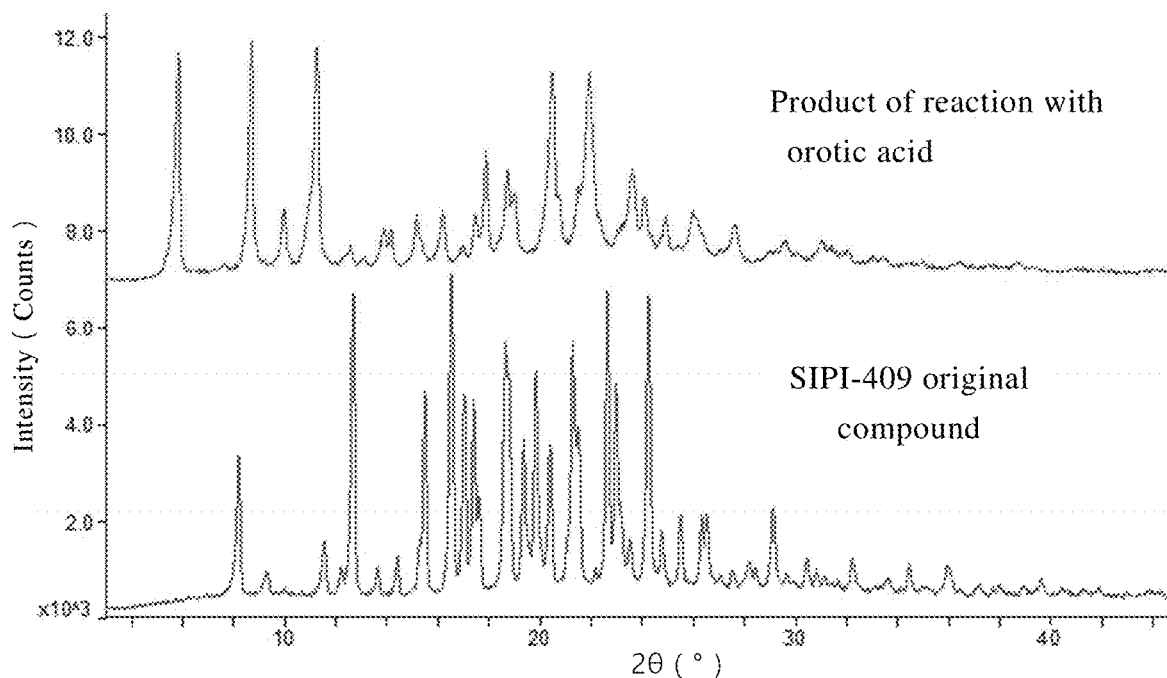
Figure 15F:
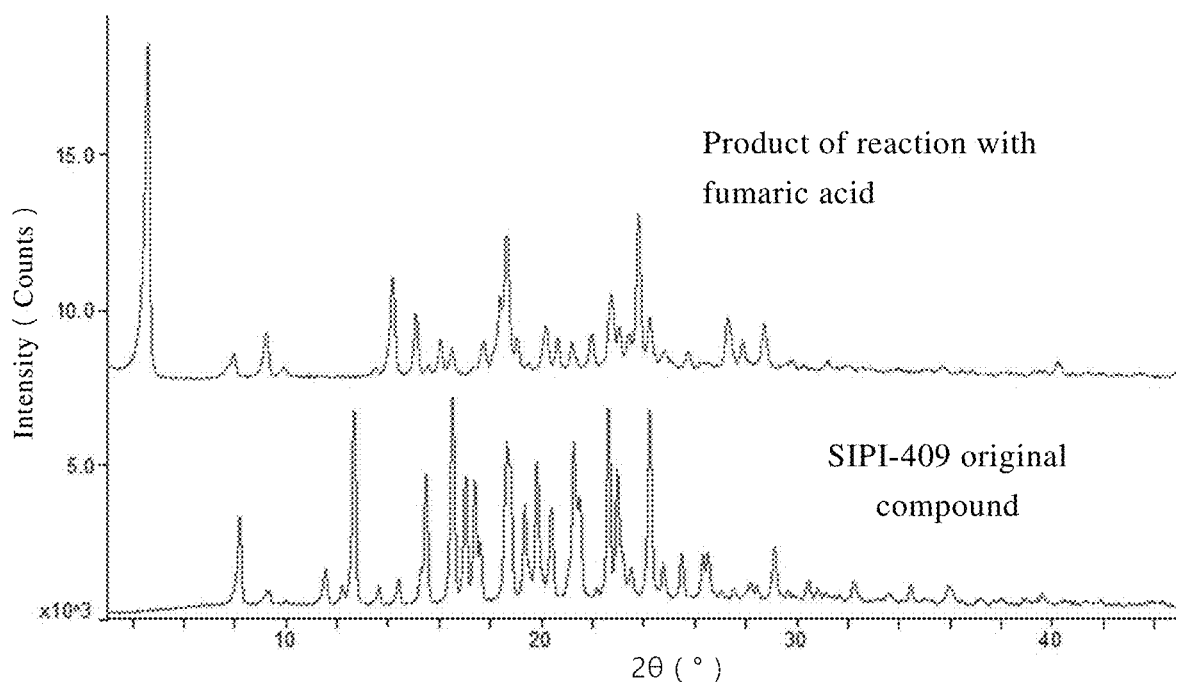
Figure 15G:
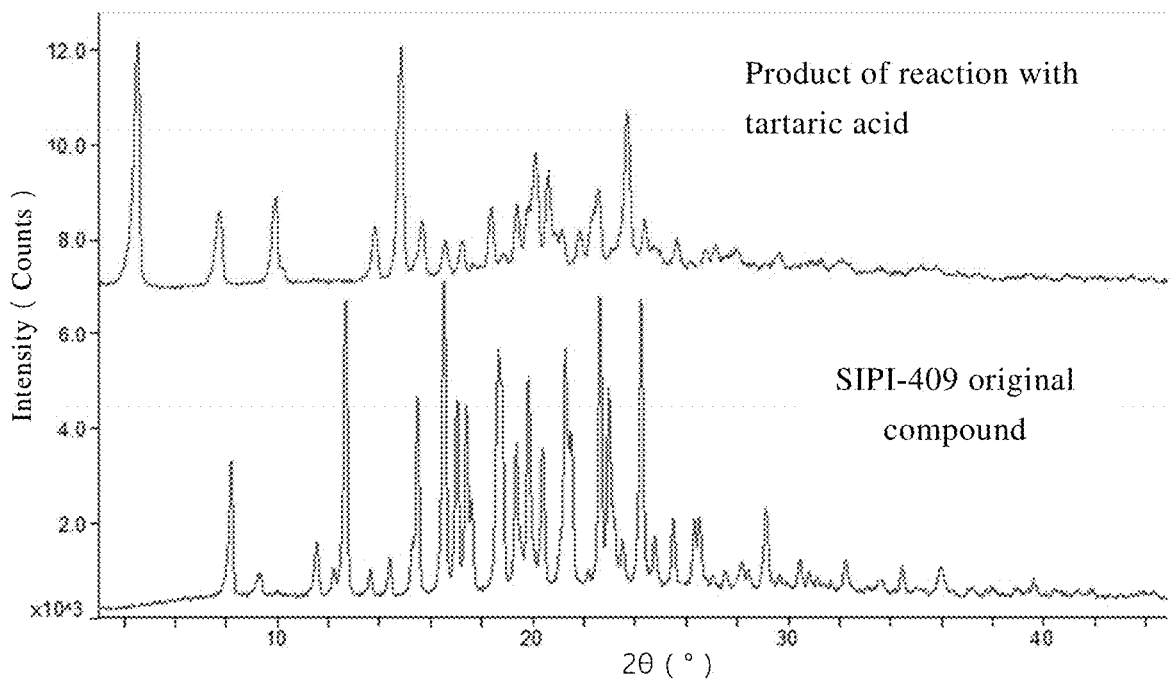
Figure 15H:
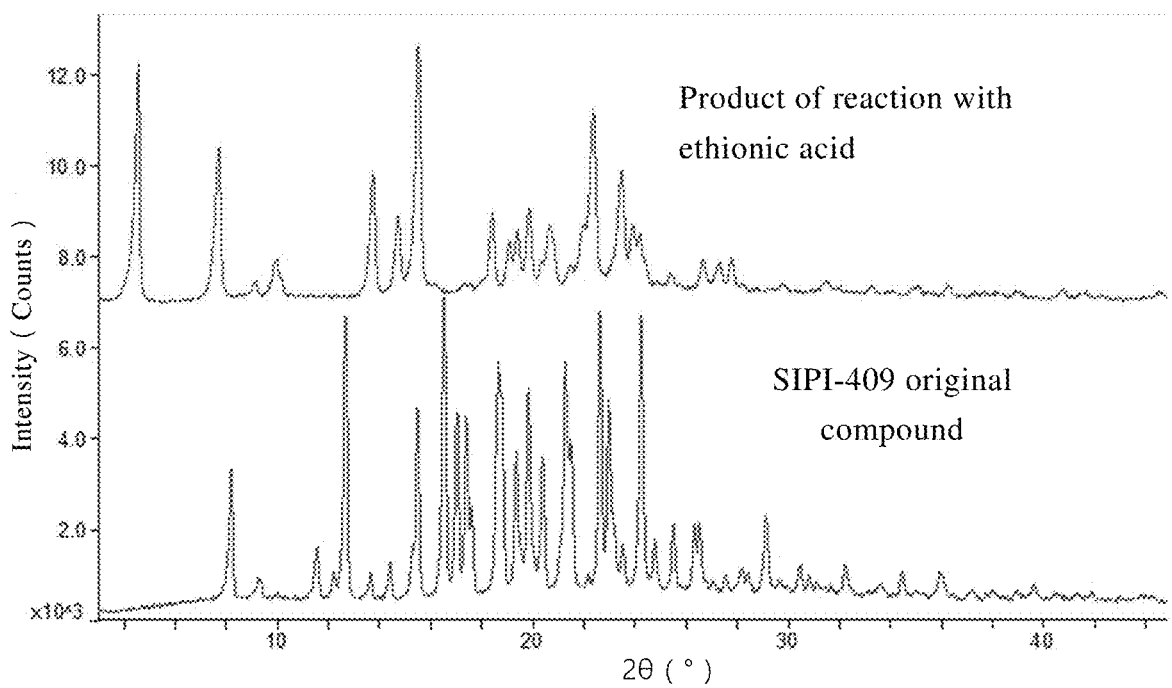
Figure 15I:
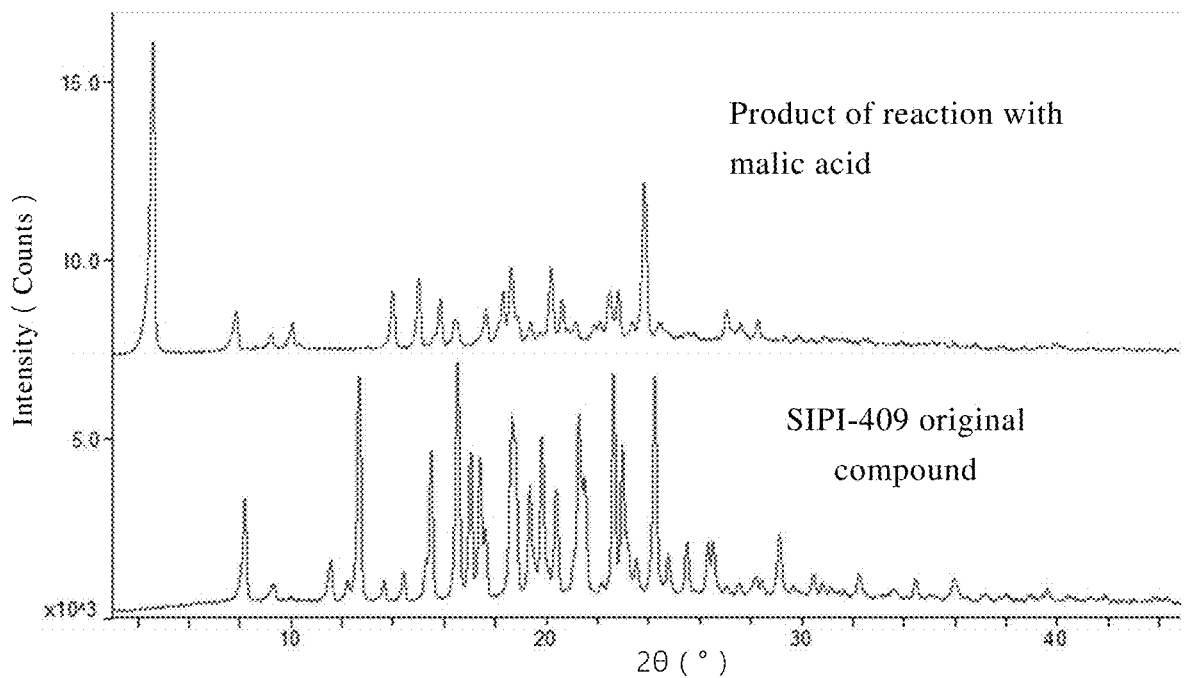
Figure 15J:
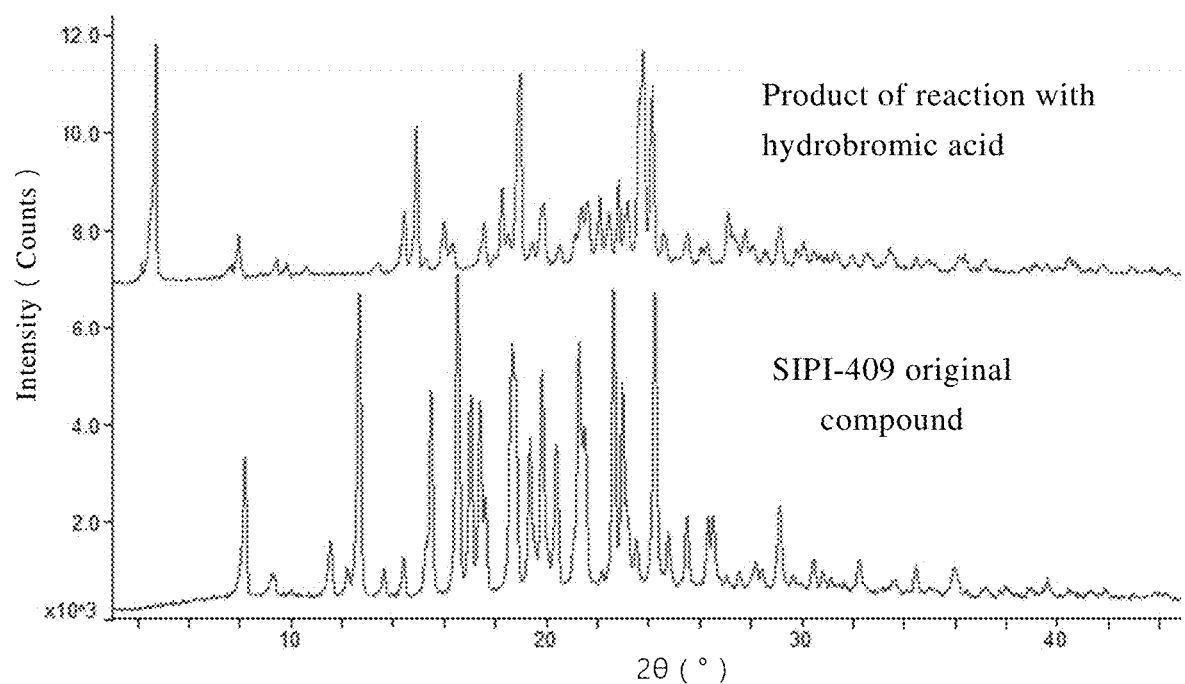
Figure 15K:
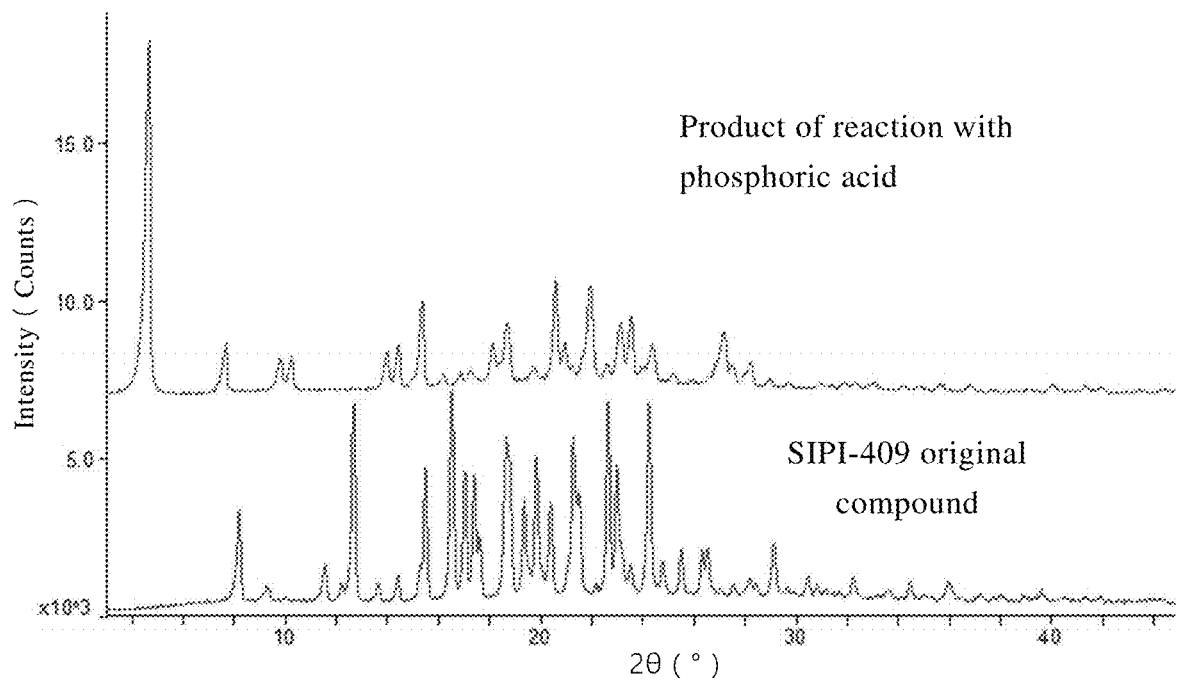
Figure 15L:
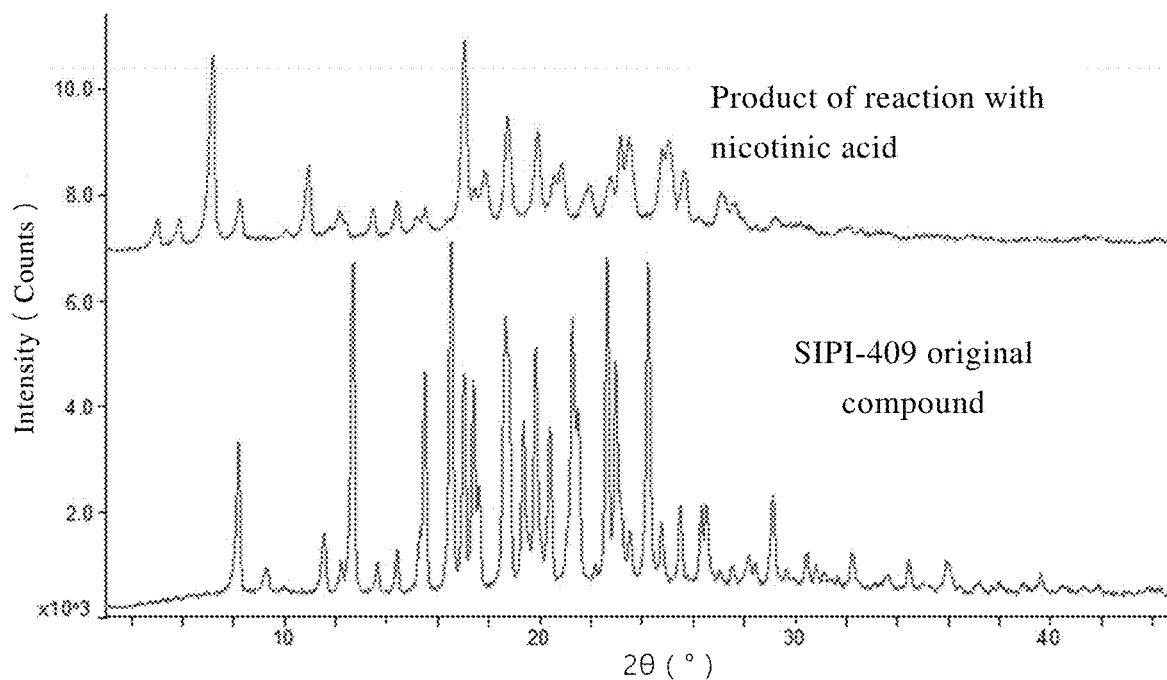
Figure 15M:
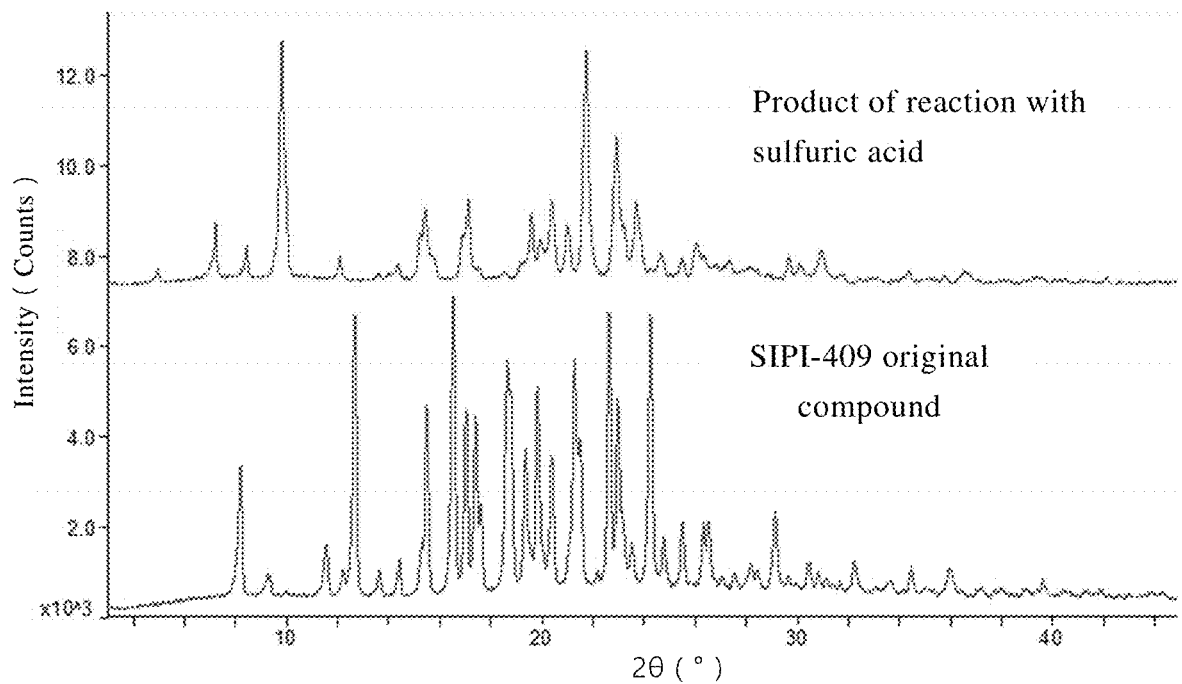
Figure 15N:
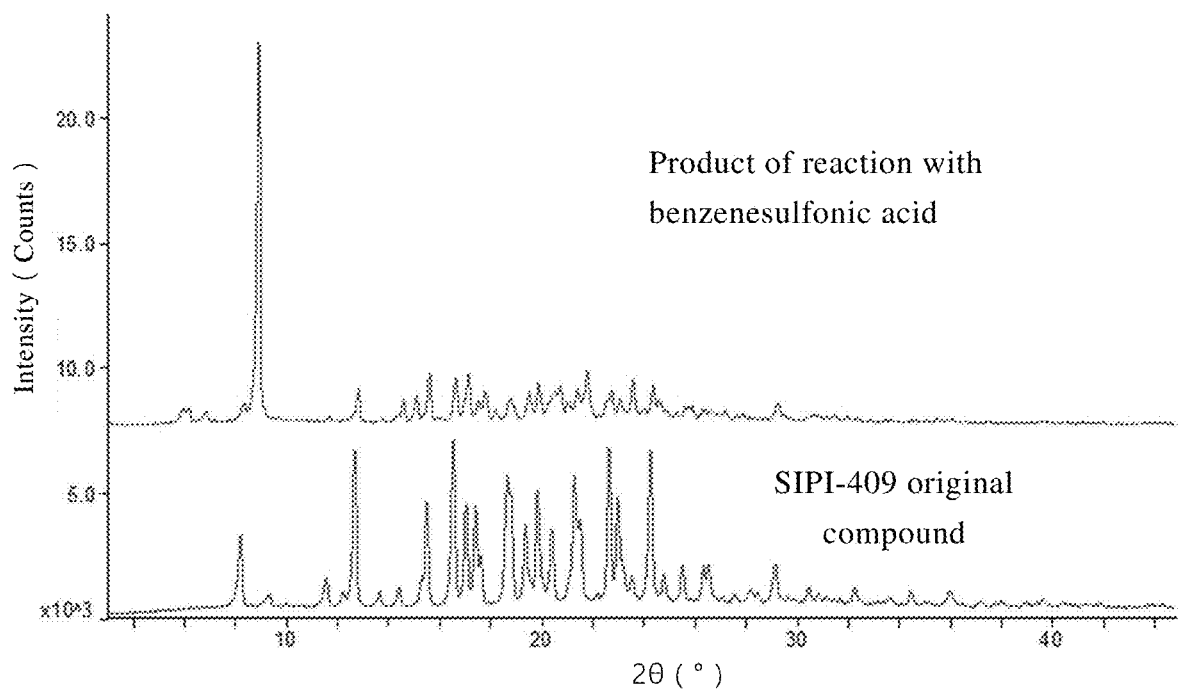

The provided SIPI-409 orotate crystal according to the present invention, as measured by differential scanning calorimetry (DSC), is observed with an endothermic peak at 138±5° C. in the DSC spectrum at a temperature rate of 10° C./min or preferably has the DSC spectrum in FIG. 14.

Crytals of the SIPI-409 salt derivatives according to the present invention include monocrystals and polymorphisms.

The present invention further provides methods for preparing the salt derivatives of SIPI-409 and crystals thereof, which comprise dissolving SIPI-409 in an organic solvent, adding an organic or inorganic acid to react under agitation, then cooling to crystallize to give the crystalline salt derivative of SIPI-409. Solvents useful here include, for example, alcohol solvents, ketone solvents, ether solvents, ester solvents, aromatic hydrocarbon solvents and nitrile solvents. Useful alcohol solvents include, for example, methanol, ethanol, and isopropanol, with methanol being preferred. Useful ketone solvents include, for example, acetone and 2-butanone. Useful ether solvents include, for example, methyl tertbutyl ether, tetrahydrofuran, and 2-methyltetrahydrofuran. Useful ester solvents include, for example, ethyl acetate, methyl acetate and isopropyl acetate. Useful aromatic hydrocarbon solvents include, for example, toluene and xylene. A useful nitrile solvent can be, for example, acetonitrile. The salt-forming reaction can be conducted at a temperature in the range of 0-80° C., preferably 10-60° C. and most preferably 40° C. The ratio of SIPI-409 to the acid and the manner of material feeding may vary depending on the desired salt derivative, without departing from the principle of the present invention.

The provided salt derivatives of SIPI-409 or crystals thereof according to the present invention are stable and useful as active ingredients in antiarrhythmic drugs for oral administration in clinic. Typical dosage forms for oral administration include, for example, normal tablets, capsules, dispersible tablets, pellets, etc., which may optionally comprise one or more auxiliary agent(s) such as excipients, lubricants and binders, etc., as commonly known in the field.

Any of the features as described in the above or the examples below can be recombined as desirable. Any of the features in the present disclosure can be used in combination with any forms of composition. For any of the features in the present disclosure, it further includes the alternatives that can provide identical, equivalent or similar effects when being used instead. Therefore, unless otherwise stated, a feature as specified herein is just an example of the equivalent or similar features in general.

Advantages of the present invention mainly include that the present invention provides novel salt derivatives of SIPI-409 and crystals thereof with significantly improved solubility in water, which further enables improved bioavailability and druggability.

The present invention will be further described below by referring to the specific embodiments. It should be understood that these examples are only provided for the purpose of illustration, without intending to limit the scope of the invention in any sense. In the following examples, experiments with no conditions given particularly were conducted under the conditions according to general practices or manufacturer's instructions. Unless otherwise stated, all percentages, ratios, proportions or parts are by weight. Herein, percent by weight/volume is expressed in the unit as commonly known and refers to, for instance, the amount of a solute by weight in a volume of 100 ml of solution. Unless otherwise defined, all the professional and scientific terms used herein have the meanings familiar to those skilled in the art. In addition, any methods and materials similar or equivalent to those as described are also useful in the present invention method. The preferred embodiments and materials described herein are merely for the purpose of illustration.

In the described experiments, the XRPD spectra were obtained under the condition using a Cu target radiation source.

In the described experiments, the DSC spectra were obtained at a temperature rate of 10° C./min.

In the context of the present invention, "stability" of a salt derivative of SIPI-40 refers to stability against heat, humidity and light, as well as hygroscopicity of the crystalline salt derivative.

Example 1

Preparation of SIPI-409 Phosphate and the Crystal Thereof 0.5 g (0.11 mmol) of SIPI-409 was placed in a 50 mL flask, to which 20 mL of methanol solvent was added, in a water-bath kept at 40° C., and then 1M phosphoric acid solution in methanol (1.3 mL, 0.13 mmol) was added drop-wise. The system was kept under agitation for 2 hrs at 40° C. and then cooled to 5-15° C. to crystallize followed by filtration. Thereby a white powder of SIPI-409 phosphate was obtained at the amount of 0.52 g and the yield of 86%. For the obtained crystal, SIPI-409:phosphoric acid=1:1, the result of elemental analysis was as set forth in Table 2, the XRPD spectrum was as set forth in FIG. 1 and the DSC spectrum as set forth in FIG. 2.

TABLE 2

Elemental Analysis:

| Analyte | Measured/% | Theoretic/% |
|---|---|---|
| C | 66.17 | 66.35 |
| H | 6.15 | 6.24 |
| N | 6.22 | 6.19 |
| S | 7.02 | 7.09 |

The values measured via elemental analysis are <0.3% different from the theoretic values.

Example 2

Preparation of SIPI-409 Sulfate and the Crystal Thereof 0.5 g (0.11 mmol) of SIPI-409 was placed in a 50 mL flask, to which 20 mL of methanol solvent was added, in a water-bath kept at 40° C., and then 1M sulfuric acid solution in methanol (1.3 mL, 0.13 mmol) was added drop-wise. The system was kept under agitation for 2 hrs at 40° C. and then cooled to 5-15° C. to crystallize followed by filtration. Thereby a white powder of SIPI-409 sulfate was obtained the amount of 0.54 g and the yield of 90%. For the obtained crystal, SIPI-409:sulfuric acid=1:1, the monocrystal parameters were as set forth in the figure, the XRPD spectrum was as set forth in FIG. 3 and the DSC spectrum as set forth in FIG. 4.

Example 3

Preparation of SIPI-409 Nicotinate and the Crystal Thereof 0.5 g (0.11 mmol) of SIPI-409 was placed in a 50 mL flask, to which 20 mL of methanol solvent was added, in a water-bath kept at 40° C., and then 0.16 g of nicotinic acid (0.13 mmol) was added. The system was kept under agitation for 2 hrs at 40° C. and then cooled to 5-15° C. to crystallize followed by filtration. Thereby a white powder of SIPI-409 nicotinate was obtained at the amount of 0.49 g and the yield of 78%. For the obtained crystal, the XRPD spectrum was as set forth in FIG. 5 and the DSC spectrum as set forth in FIG. 6.

Example 4

Preparation of SIPI-409 Oxalate and the Crystal Thereof 0.5 g (0.11 mmol) of SIPI-409 was placed in a 50 mL flask, to which 20 mL of methanol solvent was added, in a water-bath kept at 40° C., and then 0.117 g (0.13 mmol) of oxalic acid was added. The system was kept under agitation for 2 hrs at 40° C. and then cooled to 5-15° C. to crystallize followed by filtration. Thereby a white powder of SIPI-409 oxalate was obtained at the amount of 0.50 g and the yield of 84%. For the obtained crystal, the XRPD spectrum was as set forth in FIG. 7 and the DSC spectrum as set forth in FIG. 8.

Example 5

Preparation of SIPI-409 Glycolate and the Crystal Thereof 0.5 g (0.11 mmol) of SIPI-409 was placed in a 50 mL flask, to which 20 mL of methanol solvent was added, in a water-bath kept at 40° C., and then 0.098 g (0.13 mmol) of glycolic acid was added. The system was kept under agitation for 2 hrs at 40° C. and then cooled to 5-15° C. to crystallize followed by filtration. Thereby a white powder of SIPI-409 glycolate was obtained at the amount of 0.47 g and the yield of 81%. For the obtained crystal, the XRPD spectrum was as set forth in FIG. 9 and the DSC spectrum as set forth in FIG. 10.

Example 6

Preparation of SIPI-409 Benzenesulfonate and the Crystal Thereof 0.5 g (0.11 mmol) of SIPI-409 was placed in a 50 mL flask, to which 20 mL of methanol solvent was added, in a water-bath kept at 40° C., and then 0.205 g (0.13 mmol) of benzenesulfonic acid was added. The system was kept under agitation for 2 hrs at 40° C. and then cooled to 5-15° C. to crystallize followed by filtration. Thereby a white powder of SIPI-409 benzenesulfonate was obtained at the amount of 0.57 g and the yield of 84%. For the obtained crystal, the XRPD spectrum was as set forth in FIG. 11 and the DSC spectrum as set forth in FIG. 12.

Example 7

Preparation of SIPI-409 Orotate and the Crystal Thereof 0.5 g (0.11 mmol) of SIPI-409 was placed in a 50 mL flask, to which 20 mL of methanol solvent was added, in a water-bath kept at 40° C., and then 0.226 g (0.13 mmol) of orotic acid monohydrate was added. The system was kept under agitation for 2 hrs at 40° C. and then cooled to 5-15° C. to crystallize followed by filtration. Thereby a white powder of SIPI-409 orotate was obtained at the amount of 0.52 g and the yield of 77%. For the obtained crystal, the XRPD spectrum was as set forth in FIG. 13 and the DSC spectrum as set forth in FIG. 14.

Example 8

Measurement of Solubility in Water

Solubility of SIPI-409 and of the salt derivatives thereof in water was measured by liquid chromatography.

Main steps: preparing SIPI-409 standards at the concentrations of 5 μg/mL, 10 μg/mL, 50 μg/mL, 100 μg/mL, 200 μg/mL and establishing the standard curve of these preparations. The result was as set forth in FIG. 17.

Chromatography Conditions:

Chromatography column: Phenomenex Luna 5u C18(2) 100 A 4.6×200 mm

Detection wave-length: 210 nm

Mobile phase: acetonitrile/phosphate buffer (0.68 g/L monopotassium phosphate, pH was adjusted to 3.0 using triethylamine)=68/32

Column temperature: 30° C.

Load volume: 10 μL

Residence time: around 6.3 min

Sample treatment: the test samples were prepared into saturated solutions in water (suspensions) and shaken for 12 hrs at 30° C., which were further ultrasonicated for 30 s, followed by filtration and preparation of serial dilutions as appropriate, which were then analyzed by HPLC. Results were summarized in Table 3.

according to the present invention exhibited significantly increased solubility in water, compared to SIPI-409 and SIPI-409 hydrochloride.

Example 9

Pharmacokinetic Study

In view that SIPI-409 phosphate was observed with a significantly increased solubility in water compared to SIPI-409 and SIPI-409 hydrochloride in the measurement of solubility in water, it was further studied on pharmacokinetics, in comparison with SIPI-409 hydrochloride.

Experiment Method

SIPI-409 hydrochloride and SIPI-409 phosphate were administrated peros (PO), and were studied on in vivo pharmacokinetic parameters and bioavailability in SD rats. Concentrations of SIPI-409 hydrochloride and SIPI-409 phosphate in plasma were measured at intervals using Liquid Chromatography-Mass Spectrometry-Mass Spectrometry assay.

Data Processing

The obtained plasma concentration data were processed using the pharmacokinetic processing software WinNonlin 5.2 to calculate the relevant pharmacokinetic parameters according to non-compartmental model.

Experiment Results

The primary pharmacokinetics of SIPI-409 hydrochloride and SIPI-409 phosphate were as set forth in Table 4.

TABLE 4

Major Pharmacokinetic Parameters after a Single Dose of Oral Administration in SD Rats

| PO-10 mg/kg (based on SIPI-409) | $AUC_{(0-t)}$ (μg/L · h) | $AUC_{(0-\infty)}$ (μg/L · h) | $MRT_{(0-\infty)}$ (μg/L · h) | $t_{1/2}$ (h) | Tmax (h) | Cmax (μg/L) | F (%) |
|---|---|---|---|---|---|---|---|
| SIPI-409 hydrochloride | 482.88 | 503.82 | 2.71 | 1.8 | 0.33 | 191.96 | 24.63 |
| SIPI-409 phosphate | 1366.89 | 1437.93 | 4.23 | 2.66 | 0.33 | 376.24 | 79.33 |

TABLE 3

Results of solubility in water

| Compound | Solubility (nmol/mL) | Solubility (mg/mL) |
|---|---|---|
| SIPI-409 | 0.15 | 0.07 |
| SIPI-409 Hydrochloride | 1.05 | 0.51 |
| SIPI-409 Succinate | 0.28 | 0.16 |
| SIPI-409 Fumarate | 0.21 | 0.12 |
| SIPI-409 Tartarate | 0.36 | 0.22 |
| SIPI-409 Ethionate | 0.68 | 0.44 |
| SIPI-409 Glycolate | 6.08 | 3.21 |
| SIPI-409 Orotate | 3.17 | 1.93 |
| SIPI-409 Malate | 0.65 | 0.38 |
| SIPI-409 Hydrobromate | 0.83 | 0.44 |
| SIPI-409 Oxalate | 7.23 | 3.52 |
| SIPI-409 Phosphate | 17.62 | 9.69 |
| SIPI-409 Nicotinate | 7.39 | 4.26 |
| SIPI-409 Benzenesulfonate | 3.21 | 1.96 |
| SIPI-409 Sulfate | 10.47 | 5.76 |

As the results indicate, the SIPI-409 phosphate, SIPI-409 sulfate, SIPI-409 nicotinate, SIPI-409 oxalate, SIPI-409 glycolate, SIPI-409 benzenesulfonate and SIPI-409 orotate As the results indicate, in SD rats, intravenous administration of α-crystalline form of SIPI-409 phosphate provided pharmacokinetic parameters substantially comparable to SIPI-409 hydrochloride. In SD rats, via oral administration, the bioavailability was 24% for SIPI-409 hydrochloride and 79% for SIPI-409 phosphate. That is, the bioavailability of SIPI-409 phosphate according to the present invention was increased by 329% compared to SIPI-409 hydrochloride.

Example 10

Stability Investigations

Temperature Stability Investigation

Phosphate, nicotinate, glycolate, oxalate, orotate, benzenesulfonate and sulfate of SIPI-409 were placed in an oven at 60° C. XRPD measurements were carried out on samples taken out on day 0, 5, 10, 20 and 30.

Humidity Stability Investigation

The phosphate, nicotinate, glycolate, oxalate, orotate, benzenesulfonate and sulfate of SIPI-409 were kept in a 92.5% RH (saturated KNO3) atmosphere. XRPD measurements were carried out on samples taken out on day 0, 5, 10, 20 and 30.

Light Stability Investigation

The phosphate, nicotinate, glycolate, oxalate, orotate, benzenesulfonate and sulfate of SIPI-409 were placed in a light incubator. XRPD measurements were carried out on samples taken out on day 0, 5, 10, 20 and 30.

Hygroscopicity Investigation

Hygroscopicity was further investigated by placing the phosphate, nicotinate, glycolate, oxalate, orotate, benzenesulfonate and sulfate of SIPI-409 in a dynamic vapor sorption (DVS) analyzer.

Results of stability were as set forth in FIG. 18 and Table 5.

TABLE 5

Results of seven (7) SIPI-409 salt forms

| Compound | Solubility in water (mg/mL) | Stability 60° C. | Stability 92.5% RH | Stability Light | DVS Max Hygroscopicity |
|---|---|---|---|---|---|
| phosphate | 9.69 | Stable | Stable | Stable | 0.7% |
| nicotinate | 4.26 | Instable | Hygroscopic (decreased crystallinity) | Stable | 4.5% |
| glycolate | 3.21 | Stable | Stable | Stable | 0.8% |
| oxalate | 3.52 | Stable | Hygroscopic (decreased crystallinity) | Stable | 9.5% |
| orotate | 1.93 | Stable | Stable | Stable | 1.1% |
| benzenesulfonate | 1.96 | Stable | Hygroscopic (decreased crystallinity) | Stable | 4.5% |
| sulfate | 5.76 | Stable | Hygroscopic (decrease in crystallinity) | Stable | 5.2% |

As the results indicate, all the salt derivatives, except for nicotinate which was less stable against heat and degraded since day 5 at the increased temperature of 60° C., exhibited not only improved solubility in water but also fairly improved stability. Particularly, SIPI-409 phosphate had the highest solubility in water, which was as high as 9.69 mg/mL, and also satisfactory stabilities under high temperature, humidity and light, as well as a maximum hygroscopicity of only 0.7% by DVS.

Described above are just preferred embodiments of the present invention, which were provided with no intention to limit the scope of the present invention in technique. The scope of the invention in technique is defined in a broad sense by the claims of the application. Any technical entity or method, which is the same as or an equivalent variation of a claim of the invention, is deemed as being included in the scope of the claim.

What is claimed is:

1. A salt derivative of 1-(3-methanesulfonamidobenzyl)-6-methoxy,7-benzyloxy-1,2,3,4-tetrahydroisoquinoline of formula I:

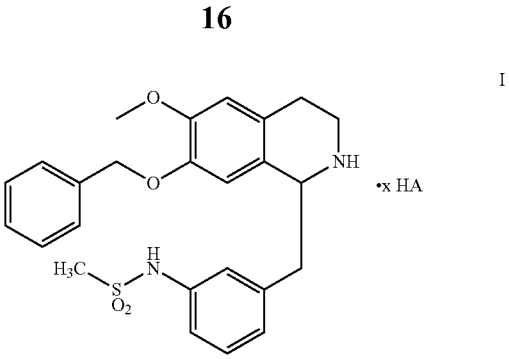

wherein the salt derivative has a solubility of no less than 3.0 nmol/mL or 1.8 mg/mL in water.

2. The salt derivative of 1-(3-methanesulfonamidobenzyl)-6-methoxy,7-benzyloxy-1,2,3,4-tetrahydroisoquinoline according to claim 1, wherein, HA is selected from the group consisting of sulfuric acid, phosphoric acid, nicotinic acid, oxalic acid, glycolic acid, benzenesulfonic acid or orotic acid, and X is ⅓, ½ or 1.

3. The salt derivative of 1-(3-methanesulfonamidobenzyl)-6-methoxy,7-benzyloxy-1,2,3,4-tetrahydroisoquinoline according to claim 2, wherein HA is sulfuric acid, and X is ½ or 1.

4. The salt derivative of 1-(3-methanesulfonamidobenzyl)-6-methoxy,7-benzyloxy-1,2,3,4-tetrahydroisoquinoline according to claim 3, wherein, when X is 1, the crystal form of said crystal is characterized by the following Bragg 2θ (Bragg 2-Theta) values as measured by X-ray powder diffraction (XRPD): 4.9±0.2°, 7.1±0.2°, 8.4±0.2°, 9.7±0.2°, 12.0±0.2°, 15.4±0.2°, 17.0±0.2°, 19.5°±0.2°, 20.3±0.2°, 20.9±0.2°, 21.6±0.2°, 22.8±0.2°, 23.6±0.2°, 24.6±0.2°, 25.4±0.2°, 26.0±0.2°, 30.8±0.2°; or by an endothermic peak at 130±5° C. in a DSC spectrum as measured by differential scanning calorimetry (DSC).

5. The salt derivative of 1-(3-methanesulfonamidobenzyl)-6-methoxy,7-benzyloxy-1,2,3,4-tetrahydroisoquinoline according to claim 2, wherein HA is oxalic acid, and X is ½ or 1.

6. The salt derivative of 1-(3-methanesulfonamidobenzyl)-6-methoxy,7-benzyloxy-1,2,3,4-tetrahydroisoquinoline according to claim 5, wherein, when X is 1, the crystal form of said crystal is characterized by the following Bragg 2θ (Bragg 2-Theta) values as measured by X-ray powder diffraction (XRPD): 3.4±0.2°, 4.6±0.2°, 5.5±0.2°, 7.8±0.2°, 9.2±0.2°, 10.2±0.2°, 10.8±0.2°, 11.9°±0.2°, 13.1±0.2°, 13.8±0.2°, 14.6±0.2°, 16.4±0.2°, 17.0±0.2°, 18.4±0.2°, 19.0±0.2°, 20.2±0.2°, 21.9±0.2°, 23.6±0.2°, 25.8±0.2°, 27.3±0.2°, 30.0±0.2°, 31.9±0.2°; or by an endothermic peak at 161±5° C. and a broad endothermic peak spanning 190-210° C. in a DSC spectrum as measured by differential scanning calorimetry (DSC).

7. A method for preparing the salt derivative of 1-(3-methanesulfonamidobenzyl)-6-methoxy,7-benzyloxy-1,2,3,4-tetrahydroisoquinoline according to claim 1, comprising: reacting 1-(3-methanesulfonamidobenzyl)-6-methoxy,7-benzyloxy-1,2,3,4-tetrahydroisoquinoline with the acid HA to form said salt derivative.

8. The method according to claim 7 for preparing the salt derivative of 1-(3-methanesulfonamidobenzyl)-6-methoxy,7-benzyloxy-1,2,3,4-tetrahydroisoquinoline, comprising: reacting 1-(3-methanesulfonamidobenzyl)-6-methoxy,7-benzyloxy-1,2,3,4-tetrahydroisoquinoline with the acid in an organic solvent to form said salt derivative.

9. The method according to claim 8 for preparing the salt derivative of 1-(3-methanesulfonamidobenzyl)-6-methoxy, 7-benzyloxy-1,2,3,4-tetrahydroisoquinoline, comprising: when HA is nicotinic acid, oxalic acid, glycolic acid, benzenesulfonic acid or orotic acid, dissolving 1-(3-methanesulfonamidobenzyl)-6-methoxy,7-benzyloxy-1,2,3,4-tetrahydroisoquinoline in an organic solvent, adding said acid, and then cooling to crystallize to give the product.

10. The method according to claim 8 for preparing the salt derivative of 1-(3-methanesulfonamidobenzyl)-6-methoxy, 7-benzyloxy-1,2,3,4-tetrahydroisoquinoline, comprising: when HA is sulfuric acid or phosphoric acid, dissolving 1-(3-methanesulfonamidobenzyl)-6-methoxy,7-benzyloxy-1,2,3,4-tetrahydroisoquinoline in an organic solvent, adding said acid in an organic solvent, and then cooling to crystallize to give the product.

11. The method according to claim 7 for preparing the salt derivative of 1-(3-methanesulfonamidobenzyl)-6-methoxy, 7-benzyloxy-1,2,3,4-tetrahydroisoquinoline, wherein, the reaction is conducted at a temperature of 0-80° C.

12. The method according to claim 8 for preparing the salt derivative of 1-(3-methanesulfonamidobenzyl)-6-methoxy, 7-benzyloxy-1,2,3,4-tetrahydroisoquinoline, wherein, said organic solvent is methanol, ethanol, isopropanol, acetone, 2-butanone, methyl acetate, isopropyl acetate, methyl tert-butyl ether acetonitrile or toluene.

13. The method according to claim 11 for preparing the salt derivative of 1-(3-methanesulfonamidobenzyl)-6-methoxy,7-benzyloxy-1,2,3,4-tetrahydroisoquinoline, wherein, when HA is phosphoric acid, the temperature of said reaction is 10-60° C.

14. A pharmaceutical composition, consisting of an effective amount of the salt derivative of 1-(3-methanesulfonamidobenzyl)-6-methoxy,7-benzyloxy-1,2,3,4-tetrahydroisoquinoline according to claim 1 and one or more pharmaceutically acceptable auxiliary agent(s).

15. A method of treating arrhythmia, comprising administering an effective amount of a composition comprising a salt derivative of 1-(3-methanesulfonamidobenzyl)-6-methoxy,7-benzyloxy-1,2,3,4-tetrahydroisoquinoline according to claim 1.

16. The salt derivative of 1-(3-methanesulfonamidobenzyl)-6-methoxy,7-benzyloxy-1,2,3,4-tetrahydroisoquinoline according to claim 2, is a crystal.

17. The salt derivative of 1-(3-methanesulfonamidobenzyl)-6-methoxy,7-benzyloxy-1,2,3,4-tetrahydroisoquinoline according to claim 16, wherein, when X is 1 and HA is phosphoric acid, the crystal form of said crystal is characterized by the following Bragg 2θ (Bragg 2-Theta) values as measured by X-ray powder diffraction (XRPD): 4.6±0.2°, 7.6±0.2°, 9.8±0.2°, 10.2±0.2°, 13.9±0.2°, 14.4±0.2°, 15.3±0.2°, 18.1±0.2°, 16.8±0.2°, 20.5±0.2°, 20.9±0.2°, 21.9±0.2°, 23.1±0.2°, 23.5±0.2°, 24.3±0.2°, 27.1±0.2°.

18. The salt derivative of 1-(3-methanesulfonamidobenzyl)-6-methoxy,7-benzyloxy-1,2,3,4-tetrahydroisoquinoline according to claim 17, wherein the X-powder diffraction spectrum of said crystal is as set forth in FIG. 1.

19. The salt derivative of 1-(3-methanesulfonamidobenzyl)-6-methoxy,7-benzyloxy-1,2,3,4-tetrahydroisoquinoline according to claim 16, wherein, when X is 1 and HA is phosphoric acid, said crystal has an endothermic peak at 201±5° C. in a DSC spectrum as measured by differential scanning calorimetry (DSC).

20. The salt derivative of 1-(3-methanesulfonamidobenzyl)-6-methoxy,7-benzyloxy-1,2,3,4-tetrahydroisoquinoline according to claim 19, wherein the DSC spectrum of said crystal is as set forth in FIG. 2.

21. The salt derivative of 1-(3-methanesulfonamidobenzyl)-6-methoxy,7-benzyloxy-1,2,3,4-tetrahydroisoquinoline according to claim 16, wherein, when HA is nicotinic acid, the crystal form of said crystal is characterized by the following Bragg 2θ (Bragg 2-Theta) values as measured by X-ray powder diffraction (XRPD): 5.0±0.2°, 5.9±0.2°, 7.2±0.2°, 8.2±0.2°, 10.9±0.2°, 12.2±0.2°, 13.4±0.2°, 14.4°±0.2°, 15.1±0.2°, 15.5±0.2°, 17.0±0.2°, 17.4±0.2°, 17.8±0.2°, 18.7±0.2°, 19.9±0.2°, 20.5±0.2°, 20.8±0.2°, 21.9±0.2°, 23.1±0.2°, 23.5±0.2°, 24.8±0.2°, 25.1±0.2°, 25.6±0.2°, 27.0±0.2°, 27.6±0.2°; or by an endothermic peak at 152±5° C. in a DSC spectrum as measured by differential scanning calorimetry (DSC).

22. The salt derivative of 1-(3-methanesulfonamidobenzyl)-6-methoxy,7-benzyloxy-1,2,3,4-tetrahydroisoquinoline according to claim 16, wherein, when HA is glycolic acid, the crystal form of said crystal is characterized by the following Bragg 2θ (Bragg 2-Theta) values as measured by X-ray powder diffraction (XRPD): 3.7±0.2°, 7.5±0.2°, 9.9±0.2°, 10.3±0.2°, 13.7±0.2°, 14.3±0.2°, 14.9±0.2°, 15.3°±0.2°, 16.1±0.2°, 16.9±0.2°, 17.6±0.2°, 18.1±0.2°, 18.9±0.2°, 19.3±0.2°, 20.4±0.2°, 20.8±0.2°, 21.8±0.2°, 22.5±0.2°, 22.9±0.2°, 24.3±0.2°, 24.9±0.2°, 25.3±0.2°, 25.9±0.2°, 27.7±0.2°; or by an endothermic peak at 187±5° C. in a DSC spectrum as measured by differential scanning calorimetry (DSC).

23. The salt derivative of 1-(3-methanesulfonamidobenzyl)-6-methoxy,7-benzyloxy-1,2,3,4-tetrahydroisoquinoline according to claim 16, wherein, when HA is benzenesulfonic acid, the crystal form of said crystal is characterized by the following Bragg 2θ (Bragg 2-Theta) values as measured by X-ray powder diffraction (XRPD): 6.1±0.2°, 6.8±0.2°, 8.2±0.2°, 8.8±0.2°, 11.5±0.2°, 12.7±0.2°, 14.4±0.2°, 15.0°±0.2°, 15.5±0.2°, 16.5±0.2°, 17.0±0.2°, 17.4±0.2°, 17.7±0.2°, 18.7±0.2°, 19.4±0.2°, 19.8±0.2°, 20.3±0.2°, 21.3±0.2°, 21.7±0.2°, 22.6±0.2°, 23.0±0.2°, 23.5±0.2°, 24.2±0.2°, 29.1±0.2°; or by an endothermic peak at 150±5° C. and a shoulder peak near 160° C. in a DSC spectrum as measured by differential scanning calorimetry (DSC).

24. The salt derivative of 1-(3-methanesulfonamidobenzyl)-6-methoxy,7-benzyloxy-1,2,3,4-tetrahydroisoquinoline according to claim 16, wherein, when HA is orotic acid, the crystal form of said crystal is characterized by the following Bragg 2θ (Bragg 2-Theta) values as measured by X-ray powder diffraction (XRPD): 5.8±0.2°, 8.7±0.2°, 9.9±0.2°, 11.2±0.2°, 12.5±0.2°, 13.9±0.2°, 14.1±0.2°, 15.2°±0.2°, 16.2±0.2°, 17.0±0.2°, 17.4±0.2°, 17.8±0.2°, 18.7±0.2°, 19.0±0.2°, 20.4±0.2°, 21.9±0.2°, 23.5±0.2°, 24.0±0.2°, 24.9±0.2°, 25.9±0.2°, 27.6±0.2°, 29.5±0.2°, 31.0±0.2°, 31.4±0.2°; or by an endothermic peak at 138±5° C. in a DSC spectrum as measured by differential scanning calorimetry (DSC).

* * * * *